(12) United States Patent
Park et al.

(10) Patent No.: US 10,912,924 B2
(45) Date of Patent: Feb. 9, 2021

(54) SYSTEMS AND DEVICES FOR CATHETER DRIVING INSTINCTIVENESS

(71) Applicant: Auris Health, Inc., Redwood City, CA (US)

(72) Inventors: June Park, San Jose, CA (US); Ray D'Ambrosio, Fremont, CA (US); Sean P. Walker, Fremont, CA (US)

(73) Assignee: Auris Health, Inc., Redwood City, CA (US)

(*) Notice: Subject to any disclaimer, the term of this patent is extended or adjusted under 35 U.S.C. 154(b) by 1420 days.

(21) Appl. No.: 14/666,866

(22) Filed: Mar. 24, 2015

(65) Prior Publication Data

US 2015/0265807 A1 Sep. 24, 2015

Related U.S. Application Data

(60) Provisional application No. 61/969,496, filed on Mar. 24, 2014, provisional application No. 61/983,191, filed on Apr. 23, 2014.

(51) Int. Cl.
*A61M 25/01* (2006.01)
*A61B 5/06* (2006.01)
(Continued)

(52) U.S. Cl.
CPC ............ *A61M 25/0133* (2013.01); *A61B 5/06* (2013.01); *A61B 5/7425* (2013.01); *A61B 34/25* (2016.02);
(Continued)

(58) Field of Classification Search
CPC .......... A61M 25/0133; A61M 25/0136; A61B 34/25; A61B 34/30; A61B 5/06;
(Continued)

(56) References Cited

U.S. PATENT DOCUMENTS

| 4,644,237 A | 2/1987 | Frushour et al. |
| 4,745,908 A | 5/1988 | Wardle |

(Continued)

FOREIGN PATENT DOCUMENTS

| CN | 1511249 | 7/2004 |
| CN | 1846181 | 10/2006 |

(Continued)

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.

(Continued)

*Primary Examiner* — Carolyn A Pehlke
*Assistant Examiner* — Victoria Fang
(74) *Attorney, Agent, or Firm* — Knobbe, Martens, Olson & Bear LLP

(57) ABSTRACT

A robotic catheter system may include a flexible catheter having a proximal end, a distal end, and an articulating portion at the distal end. It may further include a sensor coupled with the flexible catheter at or near the distal end, a visual display for displaying an image of at least part of the flexible catheter, a processor for generating a virtual indicator displayed on the image of the flexible catheter, where the virtual indicator indicates a direction of articulation and/or an amount of articulation of the articulating portion of the catheter, and a controller coupled with the proximal end of the flexible catheter to receive a user input and articulate the articulating portion of the catheter in response to the user input.

26 Claims, 18 Drawing Sheets

(51) Int. Cl.
 *A61B 5/00* (2006.01)
 *A61B 34/30* (2016.01)
 *A61B 34/00* (2016.01)
 *A61B 34/10* (2016.01)

(52) U.S. Cl.
 CPC ........ *A61B 34/30* (2016.02); *A61B 2034/102* (2016.02); *A61B 2034/301* (2016.02); *A61B 2034/742* (2016.02)

(58) Field of Classification Search
 CPC ............ A61B 5/7425; A61B 2034/102; A61B 2034/301; A61B 2034/742; Y10S 901/02; G01D 5/12–142; G05B 2219/25272; G05B 2219/37117; G05B 2219/37124; G05B 2219/37185
 USPC ........................................................ 600/424
 See application file for complete search history.

(56) References Cited

U.S. PATENT DOCUMENTS

| | | |
|---|---|---|
| 4,748,969 A | 6/1988 | Wardle |
| 4,771,262 A | 9/1988 | Reuss |
| 4,896,554 A | 1/1990 | Culver |
| 5,008,528 A | 4/1991 | Duchon |
| 5,176,310 A | 1/1993 | Akiyama et al. |
| 5,194,791 A | 3/1993 | Cull |
| 5,251,611 A | 10/1993 | Zehel et al. |
| 5,280,781 A | 1/1994 | Oku |
| 5,408,263 A | 4/1995 | Kikuchi |
| 5,499,632 A | 3/1996 | Hill et al. |
| 5,524,180 A | 6/1996 | Wang et al. |
| 5,526,812 A | 6/1996 | Dumoulin et al. |
| 5,672,877 A | 9/1997 | Liebig et al. |
| 5,762,458 A | 6/1998 | Wang et al. |
| 5,769,086 A | 6/1998 | Ritchart |
| 5,831,614 A | 11/1998 | Tognazzini et al. |
| 5,899,851 A | 5/1999 | Koninckx |
| 5,963,770 A | 10/1999 | Eakin |
| 6,004,016 A | 12/1999 | Spector |
| 6,007,550 A | 12/1999 | Wang et al. |
| 6,016,439 A | 1/2000 | Acker |
| 6,038,467 A | 3/2000 | De Bliek et al. |
| 6,096,004 A | 8/2000 | Meglan et al. |
| 6,198,974 B1 | 3/2001 | Webster, Jr. |
| 6,246,200 B1 | 6/2001 | Blumenkranz et al. |
| 6,425,865 B1 | 7/2002 | Salcudean et al. |
| 6,459,926 B1 | 10/2002 | Nowlin |
| 6,466,198 B1 | 10/2002 | Feinstein |
| 6,468,265 B1 | 10/2002 | Evans et al. |
| 6,490,467 B1 | 12/2002 | Bucholz |
| 6,516,421 B1 | 2/2003 | Peters |
| 6,690,963 B2 | 2/2004 | Ben-Haim |
| 6,690,964 B2 | 2/2004 | Bieger et al. |
| 6,837,846 B2 | 1/2005 | Jaffe |
| 6,856,827 B2 | 2/2005 | Seeley et al. |
| 7,197,354 B2 | 3/2007 | Sobe |
| 7,206,627 B2 | 4/2007 | Abovitz |
| 7,594,925 B2 | 9/2009 | Danek |
| 7,607,440 B2 | 10/2009 | Coste-Maniere et al. |
| 7,763,015 B2 | 7/2010 | Cooper et al. |
| 7,772,541 B2 | 8/2010 | Froggatt et al. |
| 7,963,288 B2 | 6/2011 | Rosenberg et al. |
| 8,180,114 B2 | 5/2012 | Nishihara et al. |
| 8,335,557 B2 | 12/2012 | Maschke |
| 8,348,931 B2 | 1/2013 | Cooper et al. |
| 8,376,934 B2 | 2/2013 | Takahashi |
| 8,396,595 B2 | 3/2013 | Dariush |
| 8,442,618 B2 | 5/2013 | Strommer et al. |
| 8,469,945 B2 | 6/2013 | Schena |
| 8,498,691 B2 | 7/2013 | Moll et al. |
| 8,506,555 B2 | 8/2013 | Ruiz Morales |
| 8,554,368 B2 | 10/2013 | Fielding et al. |
| 8,718,837 B2 | 5/2014 | Wang et al. |
| 8,720,448 B2 | 5/2014 | Reis et al. |
| 8,738,181 B2 | 5/2014 | Greer et al. |
| 8,827,948 B2 | 9/2014 | Romo et al. |
| 8,894,610 B2 | 11/2014 | MacNamara et al. |
| 8,929,631 B2 | 1/2015 | Pfister et al. |
| 8,945,095 B2 | 2/2015 | Blumenkranz et al. |
| 8,971,597 B2 | 3/2015 | Zhao et al. |
| 9,014,851 B2 | 4/2015 | Wong et al. |
| 9,023,060 B2 | 5/2015 | Cooper et al. |
| 9,057,600 B2 | 6/2015 | Walker et al. |
| 9,129,417 B2 | 9/2015 | Zheng et al. |
| 9,173,713 B2 | 11/2015 | Hart et al. |
| 9,199,372 B2 | 12/2015 | Henderson et al. |
| 9,226,796 B2 | 1/2016 | Bowling |
| 9,241,767 B2 | 1/2016 | Prisco et al. |
| 9,256,940 B2 | 2/2016 | Carelsen et al. |
| 9,271,663 B2 | 3/2016 | Walker et al. |
| 9,283,046 B2 | 3/2016 | Walker et al. |
| 9,289,578 B2 | 3/2016 | Walker et al. |
| 9,302,702 B1 | 4/2016 | Schepmann |
| 9,314,306 B2 | 4/2016 | Yu |
| 9,345,456 B2 | 5/2016 | Tsonton et al. |
| 9,358,682 B2 | 6/2016 | Ruiz Morales |
| 9,452,276 B2 | 9/2016 | Duindam et al. |
| 9,498,291 B2 | 11/2016 | Balaji et al. |
| 9,503,681 B1 | 11/2016 | Popescu et al. |
| 9,504,604 B2 | 11/2016 | Alvarez |
| 9,522,034 B2 | 12/2016 | Johnson |
| 9,532,840 B2 | 1/2017 | Wong et al. |
| 9,561,019 B2 | 2/2017 | Mihailescu et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,675,422 B2 | 6/2017 | Hourtash et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,770,216 B2 | 9/2017 | Brown et al. |
| 9,788,910 B2 | 10/2017 | Schuh |
| 9,789,608 B2 | 10/2017 | Itkowitz et al. |
| 9,818,681 B2 | 11/2017 | Machida |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,123,755 B2 | 11/2018 | Walker et al. |
| 10,130,345 B2 | 11/2018 | Wong et al. |
| 10,130,427 B2 | 11/2018 | Tanner et al. |
| 10,145,747 B1 | 12/2018 | Lin et al. |
| 10,159,532 B1 | 12/2018 | Ummalaneni et al. |
| 10,213,264 B2 | 2/2019 | Tanner et al. |
| 10,231,793 B2 | 3/2019 | Romo |
| 10,346,976 B2 | 7/2019 | Averbuch |
| 10,454,347 B2 | 10/2019 | Covington et al. |
| 10,482,599 B2 | 11/2019 | Mintz et al. |
| 10,517,692 B2 | 12/2019 | Eyre et al. |
| 10,524,866 B2 | 1/2020 | Srinivasan et al. |
| 2001/0000040 A1 | 3/2001 | Adams et al. |
| 2001/0021843 A1 | 9/2001 | Bosselmann et al. |
| 2002/0035330 A1 | 3/2002 | Cline |
| 2002/0077533 A1* | 6/2002 | Bieger .................. A61B 90/36 600/300 |

(56) References Cited

U.S. PATENT DOCUMENTS

| | | |
|---|---|---|
| 2002/0120188 A1 | 6/2002 | Brock et al. |
| 2002/0161280 A1 | 10/2002 | Chatenever et al. |
| 2002/0173878 A1* | 11/2002 | Watanabe ............. B25J 9/1638 |
| | | 700/245 |
| 2003/0045778 A1 | 3/2003 | Ohline |
| 2003/0181809 A1 | 9/2003 | Hall et al. |
| 2003/0182091 A1 | 9/2003 | Kukuk |
| 2004/0047044 A1 | 3/2004 | Dalton |
| 2004/0257021 A1 | 12/2004 | Chang et al. |
| 2004/0263535 A1 | 12/2004 | Birkenbach et al. |
| 2005/0043718 A1 | 2/2005 | Madhani |
| 2005/0065400 A1 | 3/2005 | Banik |
| 2005/0085714 A1 | 4/2005 | Foley et al. |
| 2005/0107917 A1 | 5/2005 | Smith et al. |
| 2005/0193451 A1 | 9/2005 | Quistgaard et al. |
| 2005/0222554 A1* | 10/2005 | Wallace ................ A61B 5/042 |
| | | 606/1 |
| 2005/0234293 A1 | 10/2005 | Yamamoto |
| 2005/0256398 A1 | 11/2005 | Hastings |
| 2005/0261551 A1 | 11/2005 | Couvillon |
| 2005/0272975 A1 | 12/2005 | McWeeney et al. |
| 2006/0015096 A1 | 1/2006 | Nowlin et al. |
| 2006/0041293 A1 | 2/2006 | Mehdizadeh |
| 2006/0079745 A1* | 4/2006 | Viswanathan ......... A61B 5/062 |
| | | 600/407 |
| 2006/0095022 A1 | 5/2006 | Moll et al. |
| 2006/0173290 A1 | 8/2006 | Lavallee et al. |
| 2006/0200026 A1* | 9/2006 | Wallace ................. A61B 6/12 |
| | | 600/424 |
| 2006/0200049 A1 | 9/2006 | Leo et al. |
| 2006/0258938 A1 | 11/2006 | Hoffman |
| 2007/0013336 A1 | 1/2007 | Nowlin et al. |
| 2007/0043455 A1 | 2/2007 | Viswanathan |
| 2007/0083098 A1 | 4/2007 | Stern et al. |
| 2007/0135886 A1 | 6/2007 | Maschke |
| 2007/0138992 A1 | 6/2007 | Prisco et al. |
| 2007/0142971 A1 | 6/2007 | Schena |
| 2007/0144298 A1 | 6/2007 | Miller |
| 2007/0150155 A1 | 6/2007 | Kawai |
| 2007/0185486 A1 | 8/2007 | Hauck et al. |
| 2007/0249911 A1 | 10/2007 | Simon |
| 2007/0253599 A1 | 11/2007 | White et al. |
| 2007/0287992 A1 | 12/2007 | Diolaiti |
| 2007/0299353 A1 | 12/2007 | Harlev et al. |
| 2008/0027313 A1* | 1/2008 | Shachar ............. A61B 1/00158 |
| | | 600/424 |
| 2008/0033442 A1 | 2/2008 | Amoit |
| 2008/0046122 A1 | 2/2008 | Manzo et al. |
| 2008/0082109 A1 | 4/2008 | Moll et al. |
| 2008/0097465 A1 | 4/2008 | Rollins et al. |
| 2008/0108870 A1 | 5/2008 | Wiita et al. |
| 2008/0123921 A1 | 5/2008 | Gielen et al. |
| 2008/0140087 A1 | 6/2008 | Barbagli |
| 2008/0147089 A1 | 6/2008 | Loh |
| 2008/0159653 A1 | 7/2008 | Dunki-Jacobs et al. |
| 2008/0183068 A1 | 7/2008 | Carls et al. |
| 2008/0183188 A1 | 7/2008 | Carls et al. |
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0306490 A1 | 12/2008 | Lakin et al. |
| 2008/0312771 A1 | 12/2008 | Sugiura |
| 2009/0005768 A1 | 1/2009 | Sharareh |
| 2009/0062813 A1 | 3/2009 | Prisco |
| 2009/0076534 A1 | 3/2009 | Shelton |
| 2009/0137952 A1* | 5/2009 | Ramamurthy ........... A61B 5/06 |
| | | 604/95.01 |
| 2009/0184825 A1 | 7/2009 | Anderson |
| 2009/0198298 A1 | 8/2009 | Kaiser et al. |
| 2009/0245600 A1 | 10/2009 | Hoffman |
| 2009/0248036 A1 | 10/2009 | Hoffman et al. |
| 2009/0256905 A1 | 10/2009 | Tashiro |
| 2009/0259230 A1 | 10/2009 | Khadem |
| 2009/0259412 A1 | 10/2009 | Brogardh |
| 2009/0287354 A1 | 11/2009 | Choi |
| 2009/0324161 A1 | 12/2009 | Prisco |
| 2009/0326322 A1 | 12/2009 | Diolaiti |
| 2009/0326556 A1 | 12/2009 | Diolaiti et al. |
| 2010/0019890 A1 | 1/2010 | Helmer et al. |
| 2010/0030061 A1 | 2/2010 | Canfield |
| 2010/0030115 A1 | 2/2010 | Fujimoto |
| 2010/0039506 A1 | 2/2010 | Sarvestani et al. |
| 2010/0069920 A1 | 3/2010 | Naylor et al. |
| 2010/0076263 A1* | 3/2010 | Tanaka ............... A61B 1/00006 |
| | | 600/109 |
| 2010/0121138 A1 | 5/2010 | Goldenberg et al. |
| 2010/0121269 A1 | 5/2010 | Goldenberg |
| 2010/0125284 A1 | 5/2010 | Tanner et al. |
| 2010/0161129 A1 | 6/2010 | Costa et al. |
| 2010/0168918 A1 | 7/2010 | Zhao |
| 2010/0204613 A1 | 8/2010 | Rollins et al. |
| 2010/0204713 A1 | 8/2010 | Ruiz |
| 2010/0225209 A1 | 9/2010 | Goldberg |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2010/0328455 A1 | 12/2010 | Nam et al. |
| 2011/0009880 A1 | 1/2011 | Prisco |
| 2011/0021926 A1* | 1/2011 | Spencer ............... A61B 5/0062 |
| | | 600/478 |
| 2011/0082366 A1 | 4/2011 | Scully et al. |
| 2011/0082462 A1 | 4/2011 | Suarez |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1* | 8/2011 | Donhowe ........... A61B 1/00147 |
| | | 600/102 |
| 2011/0218676 A1 | 9/2011 | Okazaki |
| 2011/0235855 A1 | 9/2011 | Smith |
| 2011/0238010 A1 | 9/2011 | Kirschenman et al. |
| 2011/0248987 A1 | 10/2011 | Mitchell |
| 2011/0257480 A1 | 10/2011 | Takahashi |
| 2011/0258842 A1 | 10/2011 | Dukesherer et al. |
| 2011/0276058 A1 | 11/2011 | Choi et al. |
| 2011/0306873 A1 | 12/2011 | Shenai et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0059392 A1 | 3/2012 | Diolaiti |
| 2012/0069167 A1 | 3/2012 | Liu et al. |
| 2012/0071752 A1 | 3/2012 | Sewell |
| 2012/0071822 A1 | 3/2012 | Romo et al. |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0123441 A1 | 5/2012 | Au |
| 2012/0130217 A1 | 5/2012 | Kauphusman et al. |
| 2012/0158011 A1 | 6/2012 | Sandhu |
| 2012/0203067 A1 | 8/2012 | Higgins et al. |
| 2012/0209293 A1 | 8/2012 | Carlson |
| 2012/0215094 A1 | 8/2012 | Rahimian et al. |
| 2012/0253276 A1* | 10/2012 | Govari ................... A61B 34/71 |
| | | 604/95.01 |
| 2012/0283745 A1 | 11/2012 | Goldberg et al. |
| 2012/0289777 A1 | 11/2012 | Chopra |
| 2012/0296161 A1 | 11/2012 | Wallace et al. |
| 2012/0302869 A1 | 11/2012 | Koyrakh |
| 2012/0314022 A1 | 12/2012 | Jo |
| 2012/0328077 A1 | 12/2012 | Bouvier |
| 2013/0018306 A1* | 1/2013 | Ludwin ................ A61B 1/0052 |
| | | 604/95.04 |
| 2013/0060146 A1 | 3/2013 | Yang et al. |
| 2013/0085330 A1 | 4/2013 | Ramamurthy et al. |
| 2013/0090530 A1 | 4/2013 | Ramamurthy |

(56) References Cited

U.S. PATENT DOCUMENTS

| | | |
|---|---|---|
| 2013/0102846 A1 | 4/2013 | Sjostrom |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle |
| 2013/0204124 A1 | 8/2013 | Duindam |
| 2013/0218005 A1 | 8/2013 | Desai |
| 2013/0303891 A1 | 11/2013 | Chopra |
| 2013/0303892 A1 | 11/2013 | Zhao |
| 2013/0317519 A1 | 11/2013 | Romo et al. |
| 2013/0325030 A1 | 12/2013 | Hourtash et al. |
| 2014/0111457 A1 | 4/2014 | Briden et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222204 A1 | 8/2014 | Kawashima |
| 2014/0222207 A1 | 8/2014 | Bowling et al. |
| 2014/0235943 A1 | 8/2014 | Paris |
| 2014/0257334 A1 | 9/2014 | Wong et al. |
| 2014/0264081 A1 | 9/2014 | Walker et al. |
| 2014/0275985 A1 | 9/2014 | Walker et al. |
| 2014/0275988 A1 | 9/2014 | Walker et al. |
| 2014/0276392 A1 | 9/2014 | Wong et al. |
| 2014/0276394 A1 | 9/2014 | Wong et al. |
| 2014/0276646 A1 | 9/2014 | Wong et al. |
| 2014/0276934 A1 | 9/2014 | Balaji et al. |
| 2014/0276937 A1 | 9/2014 | Wong et al. |
| 2014/0276938 A1 | 9/2014 | Hsu et al. |
| 2014/0277333 A1 | 9/2014 | Lewis et al. |
| 2014/0277747 A1 | 9/2014 | Walker et al. |
| 2014/0296870 A1 | 10/2014 | Stern et al. |
| 2014/0309649 A1 | 10/2014 | Alvarez et al. |
| 2014/0316420 A1 | 10/2014 | Ballard et al. |
| 2014/0343416 A1 | 11/2014 | Panescu |
| 2014/0343569 A1 | 11/2014 | Turner |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0018622 A1 | 1/2015 | Tesar et al. |
| 2015/0051592 A1 | 2/2015 | Kintz |
| 2015/0073267 A1 | 3/2015 | Brannan |
| 2015/0088161 A1 | 3/2015 | Hata |
| 2015/0101442 A1 | 4/2015 | Romo |
| 2015/0104284 A1 | 4/2015 | Riedel |
| 2015/0105747 A1 | 4/2015 | Rollins et al. |
| 2015/0119628 A1 | 4/2015 | Bharat et al. |
| 2015/0119638 A1 | 4/2015 | Yu et al. |
| 2015/0142013 A1 | 5/2015 | Tanner et al. |
| 2015/0150635 A1 | 6/2015 | Kilroy |
| 2015/0157191 A1 | 6/2015 | Phee et al. |
| 2015/0164594 A1 | 6/2015 | Romo et al. |
| 2015/0164596 A1 | 6/2015 | Romo |
| 2015/0202015 A1 | 7/2015 | Elhawary |
| 2015/0223902 A1 | 8/2015 | Walker et al. |
| 2015/0224845 A1 | 8/2015 | Anderson et al. |
| 2015/0265359 A1 | 9/2015 | Camarillo |
| 2015/0265807 A1 | 9/2015 | Park et al. |
| 2015/0290454 A1 | 10/2015 | Tyler et al. |
| 2015/0297664 A1 | 10/2015 | Kokish et al. |
| 2015/0305650 A1 | 10/2015 | Hunter |
| 2015/0311838 A1 | 10/2015 | Moule |
| 2015/0314110 A1 | 11/2015 | Park |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2015/0375399 A1 | 12/2015 | Chiu et al. |
| 2016/0000414 A1 | 1/2016 | Brown |
| 2016/0000495 A1 | 1/2016 | Elliott |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0026253 A1 | 1/2016 | Bradski et al. |
| 2016/0045269 A1 | 2/2016 | Elhawary et al. |
| 2016/0051221 A1 | 2/2016 | Dickhans et al. |
| 2016/0059412 A1 | 3/2016 | Oleynik |
| 2016/0066794 A1 | 3/2016 | Klinder et al. |
| 2016/0073928 A1 | 3/2016 | Soper |
| 2016/0075030 A1 | 3/2016 | Takahashi |
| 2016/0081568 A1 | 3/2016 | Kolberg |
| 2016/0098095 A1 | 4/2016 | Gonzalez-Banos et al. |
| 2016/0100772 A1 | 4/2016 | Ikuma |
| 2016/0128992 A1 | 5/2016 | Hudson |
| 2016/0175059 A1 | 6/2016 | Walker et al. |
| 2016/0183841 A1 | 6/2016 | Duindam |
| 2016/0184032 A1 | 6/2016 | Romo |
| 2016/0202053 A1 | 7/2016 | Walker et al. |
| 2016/0206389 A1 | 7/2016 | Miller |
| 2016/0213436 A1 | 7/2016 | Inoue |
| 2016/0213884 A1 | 7/2016 | Park |
| 2016/0228032 A1 | 8/2016 | Walker et al. |
| 2016/0256069 A1 | 9/2016 | Jenkins |
| 2016/0270865 A1 | 9/2016 | Landey et al. |
| 2016/0278865 A1 | 9/2016 | Capote et al. |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0065356 A1 | 3/2017 | Balaji et al. |
| 2017/0068796 A1 | 3/2017 | Passerini et al. |
| 2017/0100084 A1 | 4/2017 | Walker et al. |
| 2017/0100197 A1 | 4/2017 | Zubiate |
| 2017/0100199 A1 | 4/2017 | Yu et al. |
| 2017/0105803 A1 | 4/2017 | Wong et al. |
| 2017/0106904 A1 | 4/2017 | Hanson |
| 2017/0113019 A1 | 4/2017 | Wong et al. |
| 2017/0119413 A1 | 5/2017 | Romo |
| 2017/0119481 A1 | 5/2017 | Romo et al. |
| 2017/0143429 A1 | 5/2017 | Richmond et al. |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172664 A1 | 6/2017 | Weingarten et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0245854 A1 | 8/2017 | Zemlok |
| 2017/0245885 A1 | 8/2017 | Lenker |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0303889 A1 | 10/2017 | Grim |
| 2017/0304015 A1 | 10/2017 | Tavallaei et al. |
| 2017/0312481 A1 | 11/2017 | Covington |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0056044 A1 | 3/2018 | Choi et al. |
| 2018/0064498 A1 | 3/2018 | Kapadia |

(56) References Cited

U.S. PATENT DOCUMENTS

| | | |
|---|---|---|
| 2018/0078321 A1 | 3/2018 | Liao |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0090969 A1 | 3/2019 | Jarc et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0151032 A1 | 5/2019 | Mustufa et al. |
| 2019/0167361 A1 | 6/2019 | Walker et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0371012 A1 | 12/2019 | Flexman |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0206472 A1 | 7/2020 | Ma |
| 2020/0217733 A1 | 7/2020 | Lin |
| 2020/0222134 A1 | 7/2020 | Schuh |

FOREIGN PATENT DOCUMENTS

| | | |
|---|---|---|
| CN | 1857877 | 11/2006 |
| CN | 101325920 | 12/2008 |
| CN | 102316817 | 1/2012 |
| CN | 102458295 | 5/2012 |
| CN | 102711586 | 10/2012 |
| CN | 102973317 | 3/2013 |
| CN | 103565529 | 2/2014 |
| CN | 103735313 | 4/2014 |
| CN | 103767659 | 5/2014 |
| CN | 103930063 | 7/2014 |
| CN | 105559850 | 5/2016 |
| CN | 105559886 | 5/2016 |
| CN | 104931059 | 9/2018 |
| DE | 102013100605 | 7/2014 |
| EP | 1 250 986 | 10/2002 |
| EP | 1 566 150 | 8/2005 |
| EP | 1800593 A1 | 6/2007 |
| EP | 2158834 A1 | 3/2010 |
| EP | 2 392 435 | 12/2011 |
| EP | 3 025 630 | 6/2016 |
| JP | 2008-528130 | 7/2008 |
| JP | 2009-509654 | 3/2009 |
| JP | 2009-524530 | 7/2009 |
| JP | 2011-088260 | 5/2011 |
| JP | 2013-510662 | 3/2013 |
| RU | 2569699 C2 | 11/2015 |
| WO | WO 01/56457 | 8/2001 |
| WO | WO 04/029782 | 4/2004 |
| WO | WO 05/087128 | 9/2005 |
| WO | WO 06/122061 | 11/2006 |
| WO | WO 08/049088 | 4/2008 |
| WO | WO 09/120940 | 10/2009 |
| WO | WO 10/025522 | 3/2010 |
| WO | WO 11/132409 | 10/2011 |
| WO | WO 12/044334 | 4/2012 |
| WO | WO 14/114551 | 7/2014 |
| WO | WO 15/142957 | 9/2015 |
| WO | WO 17/048194 | 3/2017 |

OTHER PUBLICATIONS

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

European Extended Search Report for European Patent Application No. 15160417.0, dated Aug. 11, 2015 (6 pages).

Blankenstein, Jun. 2008, Dynamic Registration and High Speed Visual Servoing in Robot-Assisted Surgery, Katholieke Universiteit Leuven, Leuven, Belgium.

Lawton et al., 1999, Ribbons and groups: A thin rod theory for catheters and filaments, J. Phys. A., 1999, 32:1709-1735.

\* cited by examiner

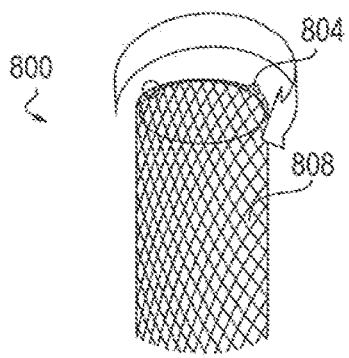 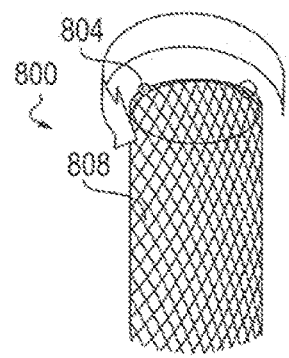
FIG. 10A  FIG. 10B
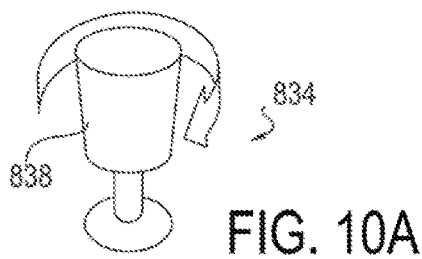 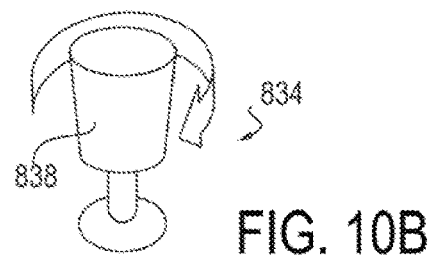
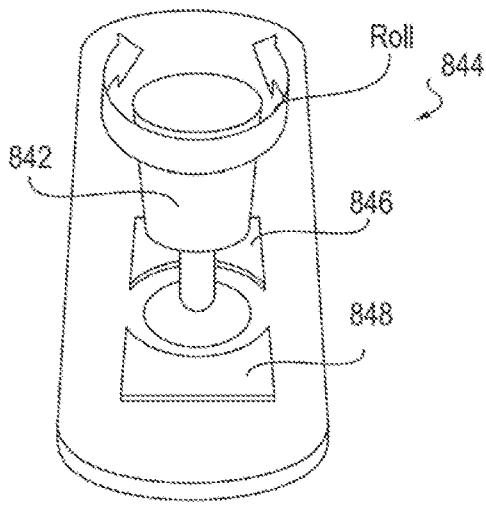 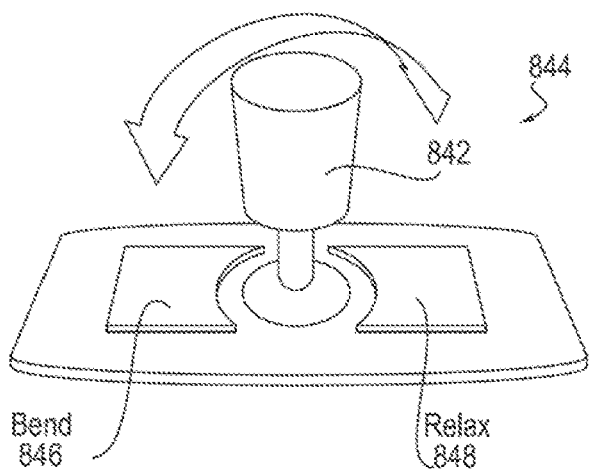
FIG. 11A  FIG. 11B
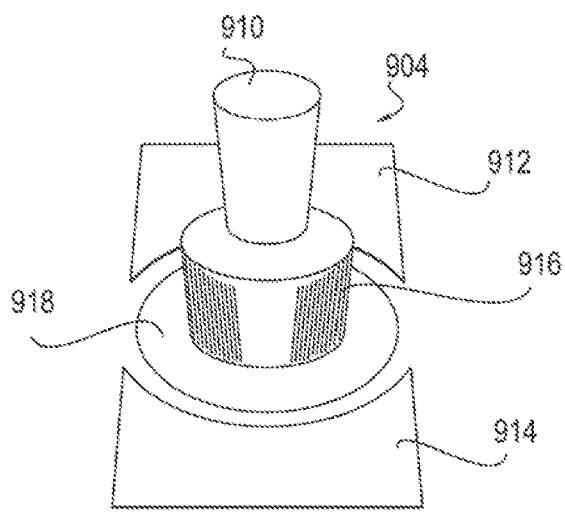
FIG. 12

SYSTEMS AND DEVICES FOR CATHETER DRIVING INSTINCTIVENESS

CROSS-REFERENCE TO RELATED APPLICATIONS

This application claims priority to U.S. provisional patent application Ser. No. 61/969,496, titled "User Interface for Catheter Control," filed Mar. 24, 2014, and U.S. provisional patent application Ser. No. 61/983,191, titled "Magnetic Encoder for the Measurement and Control of Catheter Roll," filed on Apr. 23, 2014, both of which are herein incorporated by reference in their entirety.

This application is related to U.S. patent application Ser. No. 13/452,029, titled "Balloon Visualization for Traversing a Tissue Wall," filed Apr. 20, 2012, which is herein incorporated by reference in its entirety.

TECHNICAL FIELD

The present disclosure relates generally to a robotic surgical system, and more particularly to systems and devices for improving instinctive control of catheter movement in a patient's anatomy.

BACKGROUND

Robotic surgical systems and devices are well suited for use in performing minimally invasive medical procedures, as opposed to conventional techniques that may require large incisions to open the patient's body cavity to provide the surgeon with access to internal organs. Advances in technology have led to significant changes in the field of medical surgery, such that less invasive surgical procedures, in particular minimally invasive surgery (MIS) procedures, are increasingly popular.

MIS is generally defined as surgery that is performed by entering the body through the skin, body cavity, or an anatomical opening, using small incisions rather than large, open incisions in the body. With MIS, it is possible to reduce operative trauma to the patient, hospitalization time, pain and scarring, incidence of complications related to surgical trauma, costs, and recovery time.

Special medical equipment may be used to perform an MIS procedure. Typically, a surgeon inserts small tubes or ports into a patient and uses endoscopes or laparoscopes having a fiber optic camera, light source, and/or miniaturized surgical instruments. A robotic catheter system attempts to facilitate this process by controlling the catheter tip with better precision and improved instinctive control. The goal of instinctive driving of a catheter or other elongate member is to move the catheter tip as the operator intends when the catheter is manipulated and observed by the operator remotely. For example, the orientation of the model image of the catheter is adjusted to match that of a real image of the catheter, so that a command to move the model catheter to the right results in the actual catheter tip moving to the right in the reference frame of the real image of the catheter.

However, current user interface tools and user interface devices still lack features that facilitate instinctive driving. For example, a user may desire to navigate a catheter to the right, but it may be unclear to the user which pullwire should be manipulated, especially if the catheter is experiencing some degree of roll or twist. Further, correcting or accounting for roll or twist poses challenges to instinctive driving. For example, it may not be apparent to the user if roll has occurred or what direction the catheter tip will head in after catheter roll has occurred.

In some cases, sensorizing the catheter may facilitate instinctive driving. For example, Fiber Optic Shape Sensing and Localization (FOSSL) or electromagnetic sensing may be used to sense the shape of a flexible body, such as the catheter during an MIS procedure, to permit visualization of the catheter in the patient's anatomy. The catheter position and orientation may be transmitted to a visual display to allow an operator (e.g., a surgeon) to analyze the images and make decisions to navigate through the patient's anatomy instinctively. However, this process is not straightforward and generally requires the operator to interpret multiple two-dimensional images acquired in real time (e.g., fluoroscopic images) in three-dimensional space before engaging in catheter manipulation.

Accordingly, there is a need for systems and methods to identify and/or correct catheter roll and to simplify user interface commands for more intuitive controls in order to facilitate navigation through a patient's anatomy.

BRIEF SUMMARY

In one aspect, a robotic catheter system may include: a flexible catheter having a proximal end, a distal end, and an articulating portion at the distal end; a sensor coupled with the flexible catheter at or near the distal end; a visual display for displaying an image of at least part of the flexible catheter; a processor for generating a virtual indicator displayed on the image of the flexible catheter, where the virtual indicator indicates a direction of articulation and/or an amount of articulation of the articulating portion of the catheter; and a controller coupled with the proximal end of the flexible catheter to receive a user input and articulate the articulating portion of the catheter in response to the user input.

In some embodiments, the controller may include a first control configured to receive an additional user input and rotate the virtual indicator about a longitudinal axis of the catheter in response to the additional user input, without rotating the catheter. For example, the first control may be a control column configured to rotate about an axis relative to a base of the controller, where rotation of the virtual indicator corresponds to rotation of the control column. In some embodiments, for example, rotating the control column in a clockwise direction rotates the virtual indicator in a clockwise direction when the elongate member points into the visual display, and rotating the control column in the clockwise direction rotates the virtual indicator in a counterclockwise direction when the elongate member points out of the visual display. Optionally, the system may further include an actuator coupled to the catheter for articulating the articulation portion, and the controller may include a second control coupled to the actuator for articulating the articulation portion.

In some embodiments, the virtual indicator corresponds to the controller, and inputting a user input into the controller causes the processor to generate the virtual indicator indicating a direction of movement of the articulation portion of the flexible catheter. In some embodiments, the virtual indicator corresponds to an actuator coupled to the catheter, and engaging the actuator articulates the articulating portion in a direction of the virtual indicator. In some embodiments, the virtual indicator may include a first graphic symbol corresponding to a first actuator coupled to the flexible catheter, a second graphic symbol corresponding to a second actuator coupled to the flexible catheter, and a third graphic symbol corresponding to a third actuator coupled to the flexible catheter. These graphic symbols may be equally spaced along a circumference of the image of the flexible catheter displayed on the visual display. In various embodiments the graphic symbols may be arrows, stacked bars or a combination of both.

In some embodiments, the controller may include multiple controls corresponding to the graphic symbols and coupled to the actuators, and engaging a first control articulates the elongate member in a direction of the first graphic symbol, engaging a second control bends the elongate member in a direction of the second graphic symbol, and engaging a third control bends the elongate member in a direction of the third graphic symbol. In some embodiments, engaging the first control and the second control simultaneously articulates the articulating portion of the flexible catheter in a direction between the first and second graphic symbols. In some embodiments, the controls and corresponding graphic symbols are color coded. In some embodiments, each of the graphic symbols is configured to change in size in proportion to an amount of articulation of the flexible catheter in a direction of the graphic symbols.

In various alternative embodiments, the virtual indicator may include at least one graphic symbol, such as but not limited to one or more arrows, stacked bars, ring-and-bead symbols, and/or ring-and-arrow symbols. In some embodiments, the controller includes a joystick. In some embodiments, the processor is configured to track the flexible catheter in the image using computer vision techniques. In such embodiments, the processor may be operable to overlay the virtual indicator on the image in response to tracking information.

In another aspect, a method for facilitating a robotic catheter procedure may involve generating, via a processor, a virtual indicator on a visual display, and overlaying the virtual indicator onto an image of at least an articulating portion of a flexible catheter used in the robotic catheter procedure on the visual display. The virtual indicator represents a direction of articulation and/or an amount of articulation of the articulating portion of the flexible catheter. In some embodiments, the method may further involve providing a user input device for receiving user inputs to control articulation of the articulating portion of the flexible catheter, where the user input device corresponds to the virtual indicator. Some embodiments may further involve manipulating the virtual indicator in response to a first user input, where the virtual indicator rotates about a longitudinal axis of the flexible catheter. Optionally, the method may also include articulating the flexible catheter in the direction of the virtual indicator, in response to a second user input.

In various alternative embodiments, the virtual indicator may include at least one graphic symbol, such as but not limited to an arrow, stacked bars, a ring-and-bead, and/or a ring-and-arrow. In some embodiments, the virtual indicator correlates to an actuator coupled to the flexible catheter. Some embodiments may also include engaging the actuator to articulate the articulating portion of the flexible catheter in the direction of articulation. Some embodiments may also include changing a size of the virtual indicator in response and in proportion to an amount of articulation of the articulating portion of the flexible catheter in the direction of articulation. Optionally, the method may also include tracking the flexible catheter in the image, using computer vision techniques, to generate tracking information, where the tracking information is used to overlay the virtual indicator on the image flexible catheter. The method may also optionally include registering the image of the flexible catheter with a fluoroscopic image of the flexible catheter to generate registration information, where the registration information is used to overlay the virtual indicator on the image.

These and other aspects and embodiments of the invention are described in greater detail below, in relation to the attached drawing figures.

BRIEF DESCRIPTION OF THE DRAWINGS

While the claims are not to be limited to the illustrated examples, an appreciation of various aspects is best gained through a discussion of various examples thereof. Referring now to the drawings, illustrative examples are shown in detail. Although the drawings represent the exemplary illustrations, the drawings are not necessarily to scale and certain features may be exaggerated to better illustrate and explain an innovative aspect of a given example. Further, the exemplary approaches described herein are not intended to be exhaustive or otherwise limiting or restricting to the precise form and configuration shown in the drawings and disclosed in the following detailed description. Exemplary illustrations of the present invention are described in detail by referring to the drawings as follows:

FIG. 10A a perspective view of a distal portion of a catheter arranged perpendicular to a plane of the visual display pointing into the visual display, and a side view of a joystick controller, illustrating its motion corresponding to the motion of the distal portion of the catheter, according to one embodiment;

FIG. 10B a perspective view of a distal portion of a catheter arranged perpendicular to a plane of the visual display pointing out of the visual display, and a side view of a joystick controller, illustrating its motion corresponding to the motion of the distal portion of the catheter, according to one embodiment;

FIGS. 11A and 11B are perspective and side views, respectively, of a controller of the user interface of FIG. 1B, according to one embodiment;

FIG. 12 is a perspective view of a controller of the user interface of FIG. 1B, according to an alternative embodiment;

DETAILED DESCRIPTION

Figure 1A:
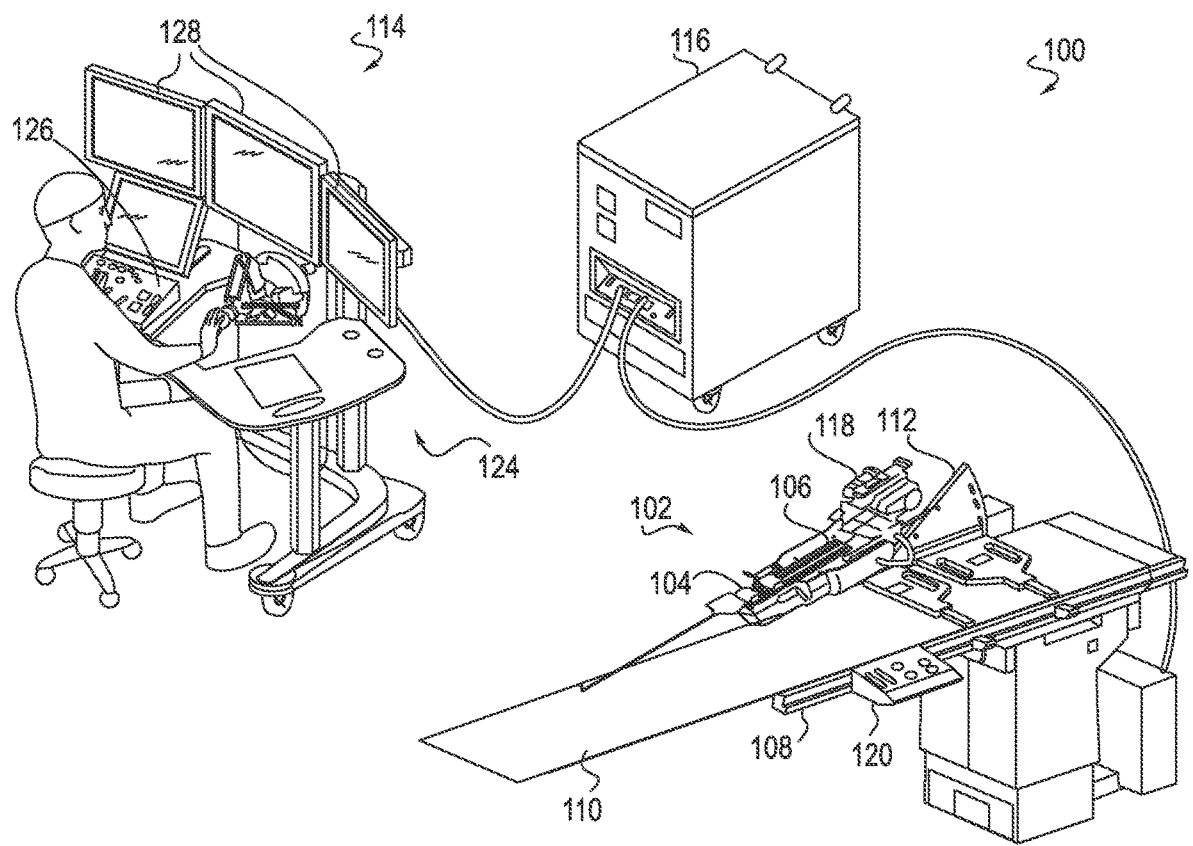
FIG. 1A is a perspective view of a robotically controlled surgical system, according to one embodiment.

Referring now to the drawings, illustrative embodiments are shown in detail. Although the drawings represent the embodiments, the drawings are not necessarily drawn to scale, and certain features may be exaggerated to better illustrate and explain innovative aspects of an embodiment. Further, the embodiments described herein are not intended to be exhaustive or otherwise limit or restrict the invention to the precise form and configuration shown in the drawings and disclosed in the following detailed description.

The disclosure describes systems and devices for improving instinctive driving of an elongate member, for example a flexible catheter. As described herein, a user interface may be configured to take advantage of catheter orientation information, such as roll and/or articulation, to provide a more intuitive controller to navigate the tortuosity of the vasculature. That is, the user interface may use information acquired from sensors, such as electro-magnetic sensors embedded into the catheter, and/or fiber optic sensors that may run the length of the catheter (e.g., FOSSL), for virtual representation of the position and orientation of the catheter within the patient's anatomy. In some embodiments, sensors may be used to determine and control catheter roll or twist to facilitate instinctive manipulation of a catheter as it is navigated through a patient's anatomy. A user interface may also use information acquired from the imaging system (e.g., such as fluoroscopy) via computer vision techniques. The disclosed user interface and roll control may take advantage of the received information to provide more intuitive commands to facilitate navigation through the patient's anatomy.

Referring now to FIG. 1A, a robotically controlled surgical system 100 may include a robotic catheter assembly 102 having a robotic or first or outer steerable component, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver"). During use, a patient is positioned on an operating table or surgical bed 110 (generally referred to as "operating table") to which robotic instrument driver 108 is coupled or mounted via a setup mount 112. Setup mount 112 may likewise include a rail system (not shown) configured to allow the setup mount 112 to translate along the length of surgical bed 110, and a motorized rail, (e.g., rail shark fin illustrated as the triangular plate) configured to tilt the instrument driver 108. As shown in FIG. 1A, system 100 includes an operator workstation 114, an electronics rack 116, a guide wire manipulator 118, and an associated bedside electronics box 120, and instrument driver 108. A surgeon is seated at operator workstation 114 and can monitor the surgical procedure, patient vitals, and control one or more catheter devices.

System components may be coupled together via multiple cables or other suitable connectors 118 to provide for data communication, or one or more components may be equipped with wireless communication components to reduce or eliminate cables 118. Communication between components may also be implemented over a network or over the Internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

The workstation 114 may include a user interface 124 configured to receive user inputs to operate various components or systems of the surgical system 100. The user interface 124 may include a controller 126 to enable the operator to control or manipulate the robotic catheter assembly 102. For instance, the controller 126 may be configured to cause the catheter to perform various tasks and/or movements (e.g., insert, retract, rotate, articulate, etc.). The controller 126 may be operable to allow the operator to navigate the catheter through the patient's anatomy via articulating the distal tip of the steerable catheter.

In some embodiments, the controller 126 may include a planar input (e.g., a joystick) and surrounding dedicated buttons configured to insert, retract, rotate, and articulate the guide wire and/or catheter, as discussed below. Additionally or alternatively, the controller 126 may include a touch screen configured to display icons corresponding to catheter and/or guide wire movements (e.g., insert, retract, roll, articulate, inflate/deflate a balloon or stent, etc.). Thus, the controller 126 may include one or more buttons, joysticks, touch screens, or other user input devices that may be desirable to control the particular component to which the controller is dedicated.

The user interface 124 may include a visual display or screen 128 configured to display information or patient-specific data to the operator located at the workstation 114. In one embodiment, the visual display 128 may be configured to display patient image data (e.g., x-ray images, MRI images, CT images, ultrasound images), physiological statistics (e.g., blood pressure, heart rate, respiratory rate), and/or patient medical records (e.g., medical history, weight, age). The visual display 128 may likewise be configured to display an image of a portion of the patient at one or more magnification levels. Additionally, the visual display 128 may be configured to receive transmissions indicating catheter position and orientation information for display. For example, the visual display 128 may be configured to display information regarding the position and/or articulation of the distal tip of a steerable catheter. Alternatively or additionally, the user interface 124 may include one or more hazard indicators (e.g., graphics, color-coding, light displays) to indicate a condition of the catheter or the system. For example, if the difference between the magnitude of commanded articulation and magnitude of measured articulation of the catheter increases beyond a threshold level, the catheter may be obstructed, for example in the vasculature, and the user may be alerted to the hazard condition of the catheter. Furthermore, the visual display 128 may be configured to display information to provide the functionalities associated with various controls of the controller 126, as discussed below. The visual display 128 may comprise one video screen, or may comprise multiple video screens working in conjunction with one another.

Figure 1B:
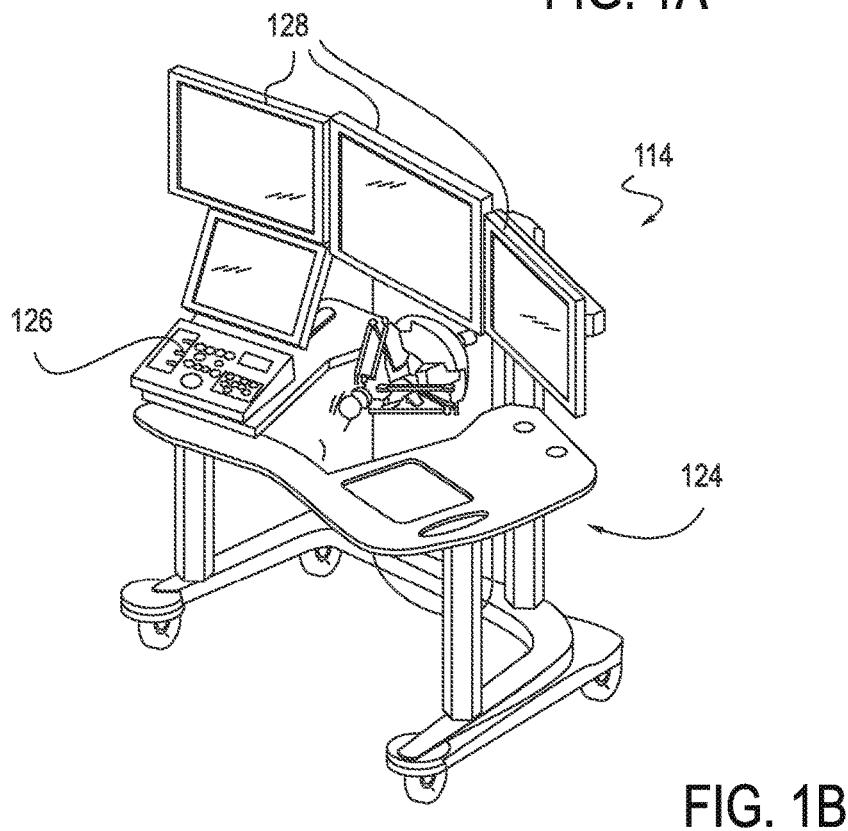
FIG. 1B is a magnified perspective view of a user interface having a controller and visual display of the robotically controlled surgical system of FIG. 1A.

FIG. 1B illustrates the workstation 114 and user interface 124 in greater detail. The user interface 124 may receive an operator input and be configured to command movement of a flexible catheter or other flexible elongate member. The user interface 114 may include the physical controller 126, with which the operator interacts, and at least one visual display 128 configured to depict an image of the elongate member, human anatomy, patient vitals, virtual indicators, etc. For example, a fluoroscopic, CT image, MRI image, or other suitable image may be displayed on the visual display 128, with a virtual overlay indicating catheter orientation, movement, and/or direction. The controller 126 may be configured to manipulate the virtual representation of the catheter on the visual display 128, which correspondingly manipulates related components of the physical catheter. That is, manipulating the controller 126 directly corresponds to manipulating the actual catheter. The workstation 114 may be located within the procedure room, or may be located remotely (e.g., in a control room, physician's office). The controller 126 may include dedicated controls configured to actuate movement of the elongate member. For example, the controller 126 may be configured to cause the catheter assembly 102 to perform various tasks and/or movements. According to another example, the controller 126 may be configured to manipulate the virtual catheter representation on the visual display 128 without likewise manipulating the physical catheter, for example in a predictive user interface, as will be discussed in detail below.

Figure 2:
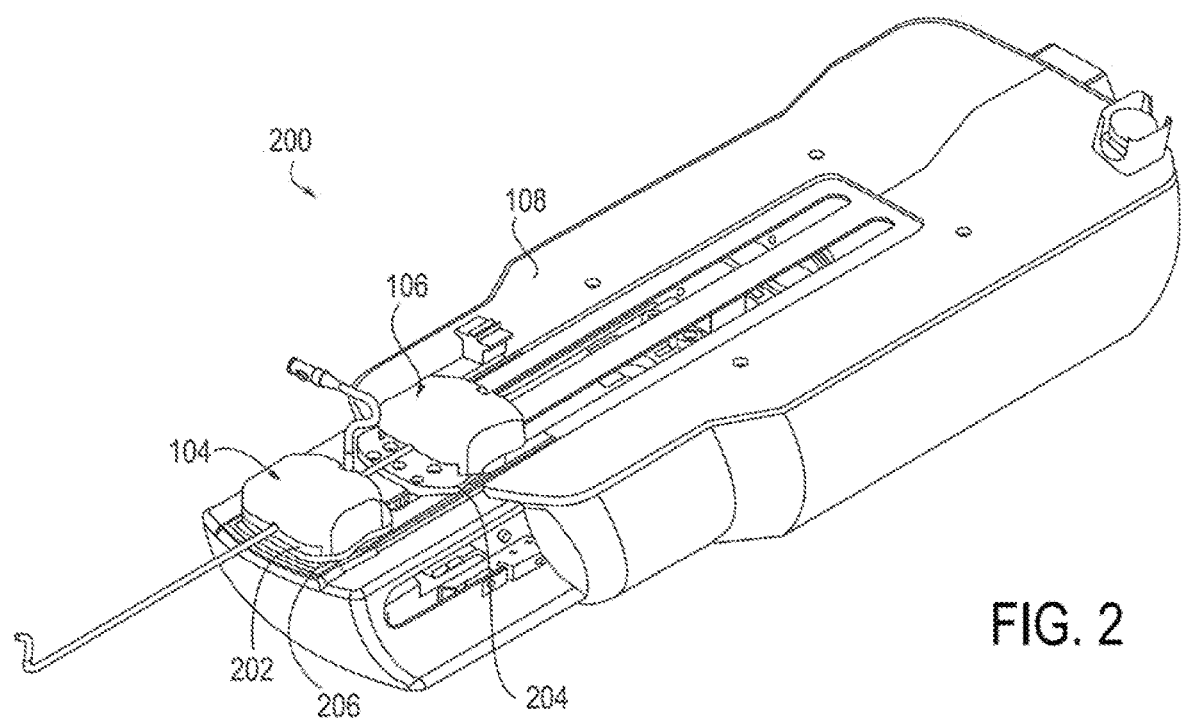
FIG. 2 is a perspective view of an exemplary catheter assembly of the surgical system of FIG. 1A.

Referring now to FIG. 2, an instrument assembly 200 for driving and/or manipulating an elongate member includes sheath instrument 104 and the associated guide or catheter instrument 106 mounted to mounting plates 202, 204 on a top portion of instrument driver 108. During use, the elongate catheter portion of catheter instrument 106 is inserted within a central lumen of the elongate sheath portion of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to mounting plates 204, 206 are driven forwards and backwards on bearings. As a result, a catheter coupled to guide catheter instrument 106 and sheath instrument 104 can be controllably manipulated while inserted into the patient, as will be further illustrated. Additional instrument driver motors may be activated to control articulation of the catheter as well as the orientation of the distal tips thereof, including tools mounted at the distal tip. Sheath catheter instrument 106 is configured to move forward and backward for effecting an axial motion of the catheter, for example to insert and retract the catheter from a patient, respectively.

Figure 3:
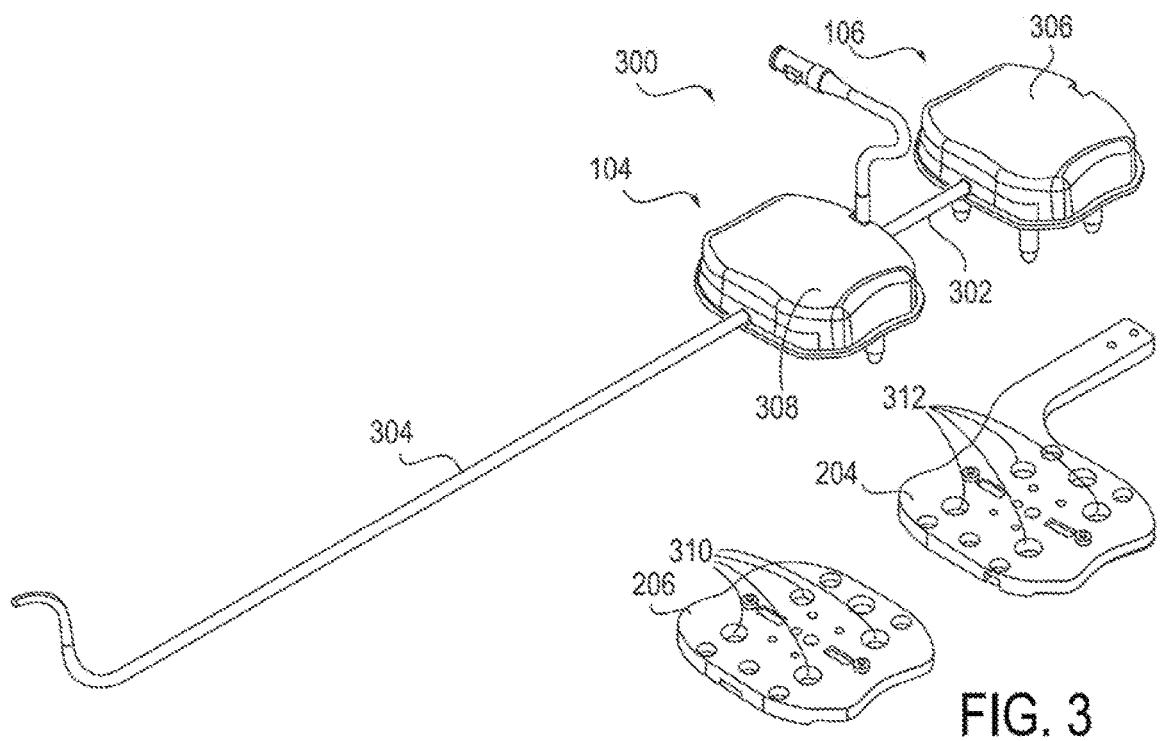
FIGS. 3 and 4 perspective views of components of the catheter assembly of FIG. 2.

Referring to FIG. 3, an assembly 300 includes sheath instrument 104 and guide or catheter instrument 106 positioned over their respective mounting plates 206, 204. In some embodiments, a guide catheter instrument member 302 is coaxially interfaced with a sheath catheter member 304 by inserting the guide catheter instrument member 302 into a working lumen of sheath catheter member 304. Sheath catheter member 304 includes a distal end that is manipulatable via assembly 300, as will be further discussed in FIG. 5. Sheath instrument 104 and guide or catheter instrument 106 are coaxially disposed for mounting onto instrument driver 108. However, in some embodiments, a sheath instrument 108 may be used without guide or catheter instrument 106, or guide or catheter instrument 106 may be used without sheath instrument 104 and may be mounted onto instrument driver 108 individually.

Figure 4:
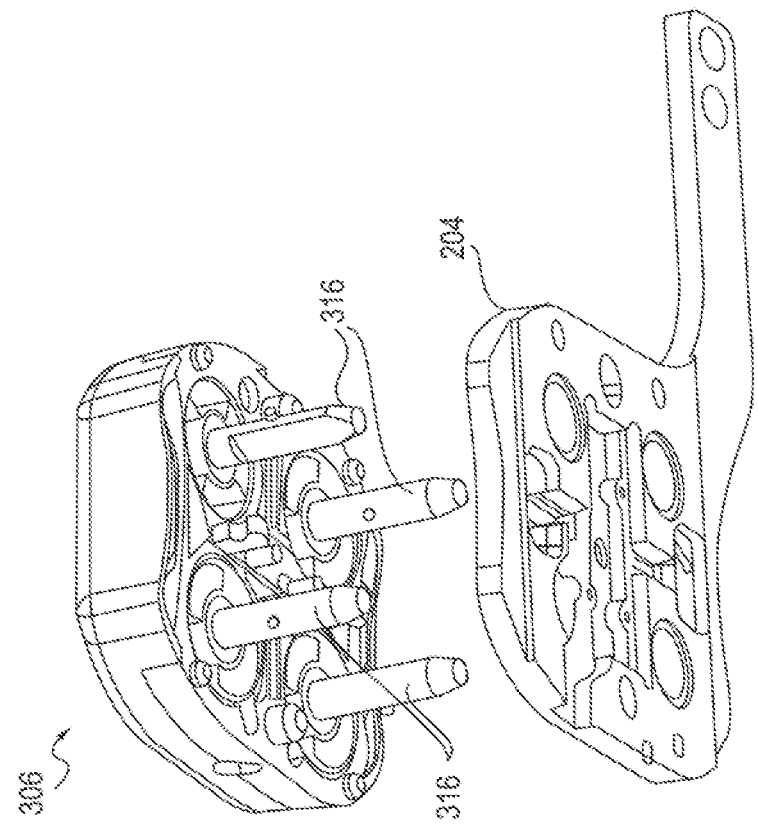
Figure 4:
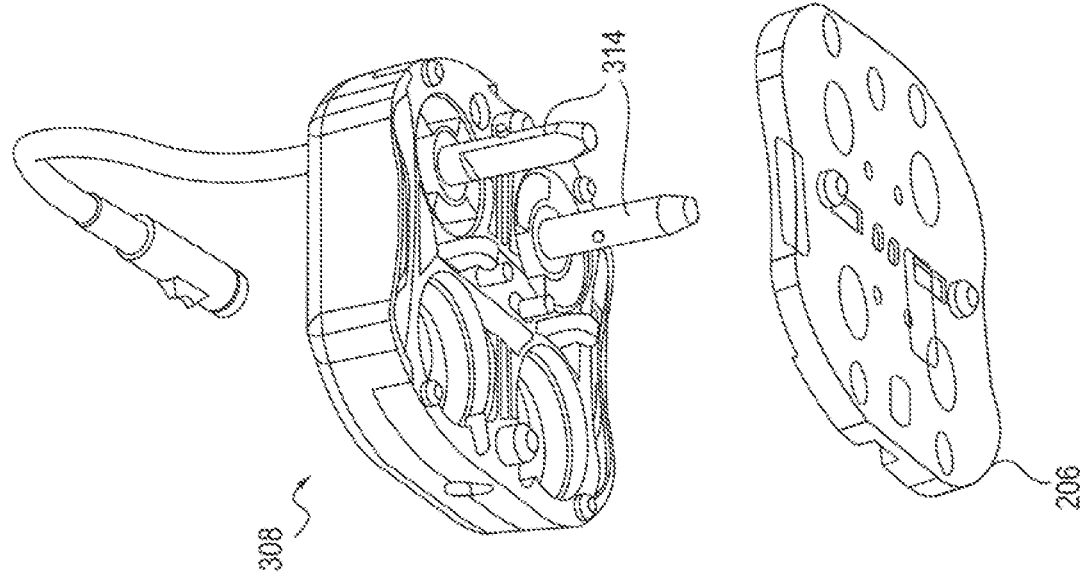

Referring to FIG. 4, when a catheter is prepared for use with an instrument driver, its splayer is mounted onto its appropriate interface plate. In this case, sheath splayer 308 is placed onto sheath interface plate 206 and a guide splayer 306 is placed onto guide interface plate 204. In the illustrated example, each interface plate 204, 206 has respectively four openings 310, 312 that are designed to receive corresponding drive shafts 314, 316. FIG. 4 illustrates an underside perspective view of shafts 314, 316 attached to and extending from the pulley assemblies of the splayers 308, 306.

Figure 5:
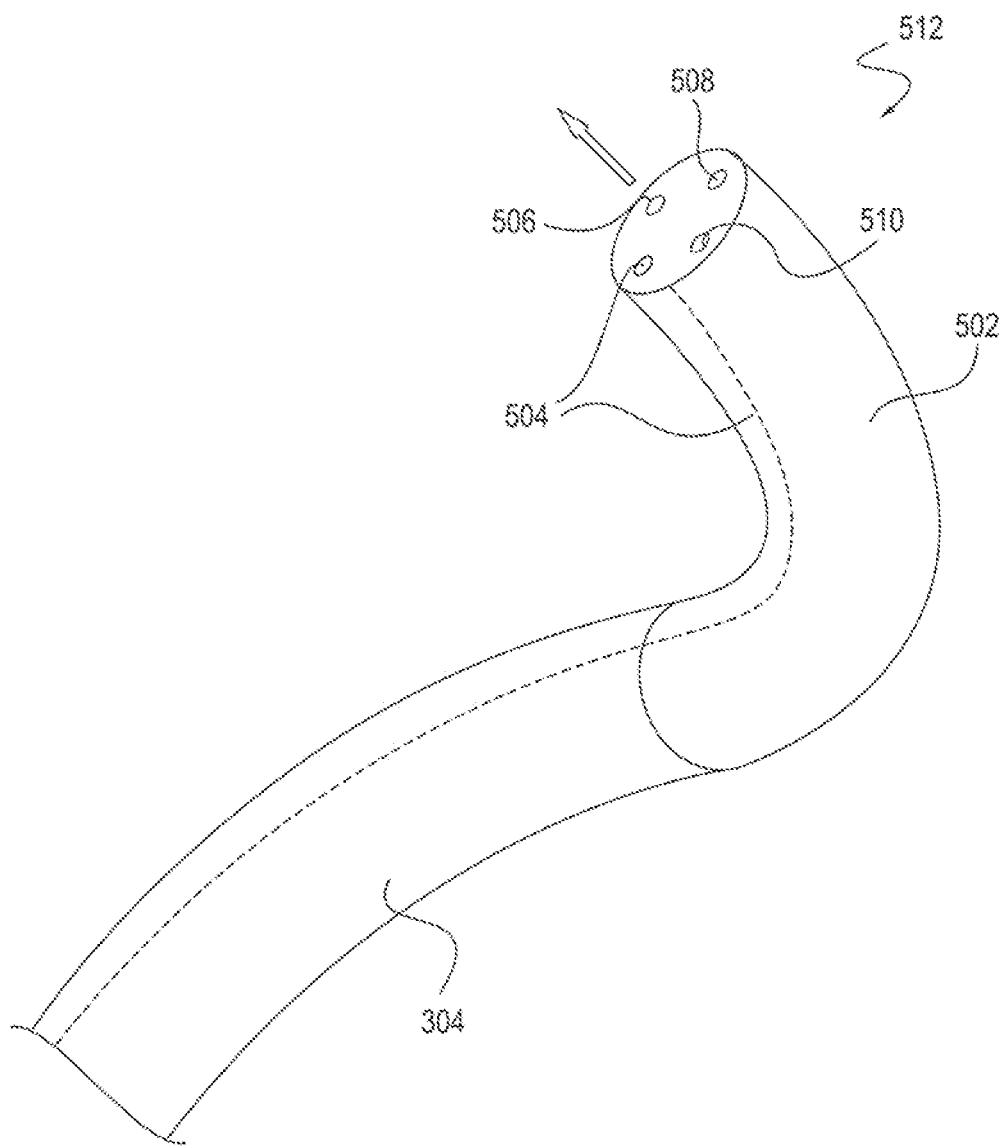
FIG. 5 a perspective view of a distal end of an exemplary catheter that is controllable by internal control elements, according to one embodiment.

Further, as shown in FIGS. 3-5, a sheath instrument 104 may include a sheath splayer 308 having drive shafts 314. Catheter instrument 106 may include a guide splayer 306 having drive shafts 316. Drive shafts 316 are each coupled to a respective motor within instrument driver 108 (motors not shown). When 4-wire catheter 304 is coupled to instrument driver 108, each drive shaft 316 thereof is thereby coupled to a respective wire 504, 506, 508, 510, as shown in FIG. 5. As such, a distal end 502 of catheter 304 can be articulated and steered by selectively tightening and loosening wires 504, 506, 508, 510. Typically, the amount of loosening and tightening is slight, relative to the overall length of catheter 304. For example, each wire 504, 506, 508, 510 typically need not be tightened or loosened more than perhaps a few centimeters.

Referring to FIG. 5, the operator workstation 114 may include a computer monitor to display a three dimensional object, such as an image 512 of a catheter instrument 304. Catheter instrument 304 may be displayed within or relative to a three-dimensional space, such as a body cavity or organ, for example a chamber of a patient's heart or a femoral artery of a patient. In one embodiment, an operator uses a computer mouse to move a control point around the display to control the position of catheter instrument 304.

User Interface for Instinctive Catheter Control

Figure 6A:
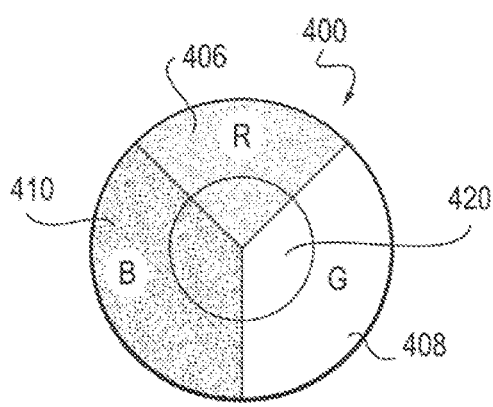
FIG. 6A is a top view of a controller with button controls, according to one embodiment.
Figure 6B:
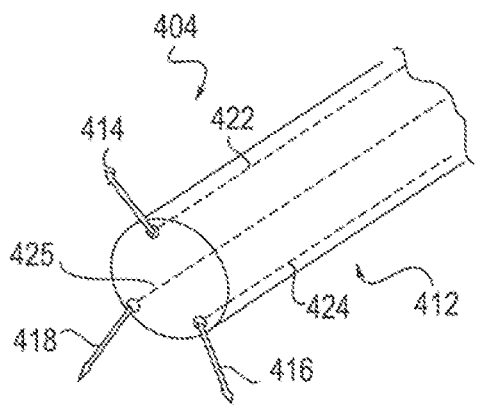
FIG. 6B is a perspective view of a catheter with a virtual indicator overlay, according to one embodiment.
Figure 6C:
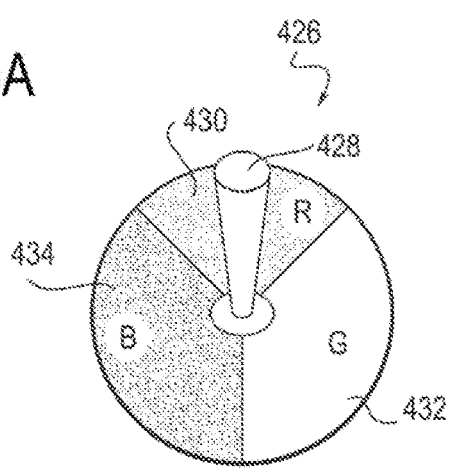
FIG. 6C is a top view of a controller with a joystick control, according to an alternative embodiment.

Referring to FIGS. 6A-6C, in one embodiment, a controller 400 (FIG. 6A) for manipulating/articulating a catheter 412 (FIG. 6B) may include a first control 406, a second control 408, and a third control 410. Each control 406, 408, 410 may include a visual identifier, such as alphabetical letters A, B, and C, colors such as red, green, and blue, and/or the like, for convenience of the operator. Referring to FIG. 6I, visual display 404 may depict an elongate member, such as a distal portion of a catheter 412 (or "catheter tip"). In this embodiment, the visual display shows the distal portion of the catheter 412, with three pull wires 422, 424, 425 and a virtual indicator overlay displaying on the catheter 412. In this embodiment, the virtual indicator overly includes three virtual indicators 414, 416, and 418 (or "graphic symbols"), which are arrows in the embodiment shown but may be stacked bars or other direction indicators in other embodiments. Each of the virtual indicators 414, 416, and 418 corresponds to one of the controls 406, 408, 410 and one of the pull wires 422, 424, 425. In some embodiments, the image of the catheter 412 may be an image acquired via any suitable medical imaging technique, such as but not limited to fluoroscopy, magnetic resonance imaging (MRI), ultrasonography, computed tomography (CT), or the like. Alternatively, the image of the catheter 412 may be a computer generated image.

The virtual indicators 414, 416, 418 are computer-generated images overlaid onto the image of the catheter 412 to illustrate a commanded movement of the catheter 412, a measured movement of the catheter 412, a difference between the two, or some combination thereof. Again, each of the virtual indicators 414, 416, 418 corresponds to one of the controls 406, 408, 410 and also one of three pull wires 422, 424, and 426 configured to manipulate and/or steer the catheter 412. In some embodiments, the virtual indicators 414, 416, 418 and the controls 406, 408, 410 may be color coded to match one another. Each control actuation, for example pressing the green button, will result in a tensioning a wire that articulates the catheter in a corresponding direction—e.g., the green arrow direction in this example. In some embodiments, fewer or greater amounts of buttons and/or wires may be used. For example, a catheter may include 0 to 5 wires or 5 to 10 wires, or any subrange between those ranges. In one embodiment, a catheter includes 4 wires. In some embodiments, a controller may include 0 to 5 or 5 to 10 buttons or controls or any subrange between those ranges. In one embodiment, a controller includes 4 buttons or controls. In some embodiments, the button-to-wire ratio remains fixed throughout the procedure (e.g., 1:1 button to wire relationship).

As mentioned above, in various embodiments, the visual display 404 and virtual indicators 414, 416, 418 may show a commanded movement of the catheter 412, a measured movement of the catheter 412, a difference between the two, or some combination thereof. "Commanded movement" or "commanded value" is intended to mean the direction (and in some embodiments the amount) of catheter movement directed by a user via the controls 406, 408, 410. "Measured movement" or "measured value" is intended to mean the direction (and in some embodiments the amount) of catheter movement measured by the system 100, for example via a sensor (or multiple sensors) on the catheter. In some embodiments, for example, the visual display 404 may show a user the direction in which the catheter 412 has been commanded to articulate, an amount of commanded articulation in the commanded direction, and also a direction and amount of actual, measured articulation of the catheter. This type of information allows the user to see how the instructed/commanded movements have translated into actual/measured movements. As discussed further below in terms of several alternative embodiments, the visual display 404 may provide this information using any of a number of different types of visual indicators 414, 416, 418, such as arrows of different sizes and shapes, stacked bars having sizes and numbers corresponding to amounts of commanded articulation of a catheter, and the like. The overlay of indicators onto an image of a catheter to provide information about catheter movement to a user may be very advantageous in providing an intuitive catheter driving experience for the user.

In some embodiments, the visual display 404 of the user interface may be configured to display information near the tip of the depicted catheter 412 so that the information stays within the operator's field of vision at all times of the procedure, unless turned off explicitly. As such, a virtual representation may overlay an imaged catheter 412 on the visual display 404 (e.g., a viewing screen), which includes virtual indicators 414, 416, 418 corresponding to visual identifiers disposed on the controls 406, 408, and 410. The visual display 404 may illustrate which direction the catheter will articulate in response to actuating a control corresponding to the virtual indicator. For example, the green arrow may indicate the catheter will move radially in the depicted direction with respect to an axis in a plane of the visual display 404.

In some embodiments, a processor (not shown) may be configured for generating the virtual representation of the catheter 412 using kinematic, FOSSL, electro-magnetic information, or imaging information acquired by computer vision techniques, for example, regarding the catheter. The processor may be configured to superimpose the virtual indicators 414, 416, 418 over the tip of the catheter 412. For instance, virtual indicators 414, 416, 418 may overlay a fluoroscopic or like image of the catheter 412 inserted in the patient's anatomy, such that the visual display 404 shows the fluoroscopic image with the virtual indicator overlay to improve instinctive navigation of the catheter. Further, the processor may be configured to adjust the virtual indicators 414, 416, 418 with corresponding movements of the catheter, such that the indicators 414, 416, 418 overlay the catheter 412 in proper position/orientation as the catheter 412 moves within the patient's anatomy. For example, if the catheter 412 rolls or twists during navigation, the virtual indicators 414, 416, 418 may adjust accordingly, such that the user always knows which wire to manipulate to drive the catheter 412 to the desired location in the vasculature. In some embodiments, a non-transitory medium (not shown), storing a set of instructions may be configured to superimpose the virtual indicators 414, 416, 418 over a fluoroscopic image of the catheter 412. The instructions may additionally be operable to allow an operator to manipulate the catheter 412 via input from the controller 400. In some embodiments, the instructions may be updated periodically to account for changes in catheter orientation and/or position, for example if the catheter 412 rolls or twists during navigation.

In some embodiments, as shown in FIG. 6A, the controller 400 may include a planar input device, such as control buttons 406, 408, 410, as described above. The button-to-wire relationship may be fixed throughout the entire procedure, such that a particular button press may always cause a particular wire to be pulled—for example, pressing the green button will always pull the green wire, regardless of catheter 412 orientation on the visual display 404. Further, in some embodiments, the controller 400 may include three button controls 406, 408, and 410, corresponding to the three pull wires 422, 424, 425 in the catheter 412, for example as represented by the three virtual indicators 414, 416, and 418 as shown in FIG. 6B. Pressing the control button 408 correspondingly actuates the pull wire 424 associated with virtual indicator 416. As shown in FIG. 6A, the controller 400 may optionally include a fourth control 420 configured to release or relax the pull wires 422, 424, 425 and thereby relax the catheter 412 to a straight position. In one alternative embodiment (not shown), each control button may include two separate buttons, in which the inner button would release the pull wire associated with the controller and hence relax the catheter (e.g., relaxing red button would relax the red wire). The outer button would pull or tension the wire to articulate the catheter in the direction of the virtual indicator.

The control buttons 406, 408, 410, and/or 420 may be touch sensitive, such that the harder a button is pushed or the more force exerted on the button, the more the button will actuate, pull, or tension the corresponding pull wire 422, 424, 425. Thus, a button pushed fully to the base of the controller 400 may pull the corresponding wire to the maximum, so that the catheter 412 is articulated maximally in the direction of the pulled wire 422, 424, 425.

Further, the control buttons 406, 408, 410 may be combined or actuated simultaneously to articulate the catheter 412 in a direction that lies in between two pull wires 422, 424, 425. For example, still referring to FIG. 6A, if control buttons 406 and 408 are pushed together, the system would pull wires 422 and 424, associated with indicators 414 and 416, thereby making the catheter 412 articulate in a direction between pull wires 422 and 424.

Referring now to FIG. 6C, in some embodiments, a controller 426 may include a control column or joystick 428 operable to gradually move about the base of the controller 426. In some embodiments, the controller 426 may include the joystick 428 and visual identifiers 430, 432, 434 on the controller 426 base, which indicate direction and/or corresponding virtual indicators and pull wires 422, 424, 425. For example, the graphics may relate to the virtual indicators 414, 416, 418 on the visual display 404 as well as the pull wires 422, 424, 425 running through the catheter 412 to perform movements. Further, as an analog device, the joystick 428 can move gradually between adjacent buttons to mimic either single or simultaneous control button input, and the articulation direction of the catheter would thereby vary smoothly between wires. The joystick 428 may be arranged concentrically with respect to the pie-shaped graphic drawing (e.g., analogous to the three button controller 400). The graphics 430, 432, and 434 suggest which pull wire 422, 424, 425 will be pulled if the joystick 428 is moved in a particular direction.

In one embodiment, the joystick 428 may include a return, for example a spring. Alternatively, the joystick 428 may not be loaded with a return, which means the joystick 428 will not return to the center when external force is removed. For example, the joystick 428 may be a position control device that maintains its tilt or orientation when released or external force on the joystick is removed. In some embodiments, the joystick 428 in a straight up, vertical, or perpendicular position relative to the controls may be equivalent to the catheter being fully relaxed, while the full forward position of the joystick (e.g., in relation to FIG. 6C, fully forward on graphic 430) means the wire associated with 430 is pulled or tensioned to the maximum, so that the catheter 412 is articulated maximally in the 430 direction. Stated alternatively, if red is the indicator associated with 430, pushing or manipulating the joystick 428 fully towards red will pull or tension the red wire 422 maximally, so the catheter 412 is articulated maximally in the red direction, as indicated by a red virtual marker 414 on the visual display 404. Advantageously, a controller 426 with a joystick 428 enables the operator to easily determine how much effort was required for tensioning each wire 422, 424, 425, by observing the orientation or position of the joystick 428. Further, the joystick 428 indicates the degree of effort the controller 426 attempts to effectuate catheter articulation. For example, if the joystick 428 is only slightly offset from center, then minimal effort may be exerted in pulling or tensioning the wire. Alternatively, if the joystick 428 is fully actuated, then full force may be exerted on the wire and the catheter 412 is maximally articulated, e.g., in the current environment. However, while the controller may exert maximum effort in attempting to articulate the catheter 412, the catheter 412 itself may not articulate, if there is an obstruction from the human anatomy and/or if the catheter 412 is experiencing roll or twist, for example.

Figure 7A:
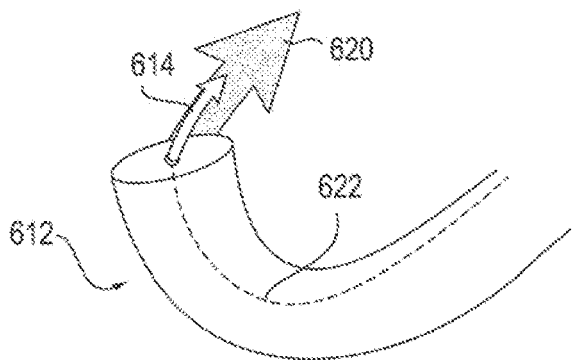
FIG. 7A is a perspective view of an articulating distal portion of a catheter and top views of the controllers of FIGS. 6A and 6C, illustrating user input corresponding to the articulation of the distal portion, according to one embodiment.
Figure 7A:
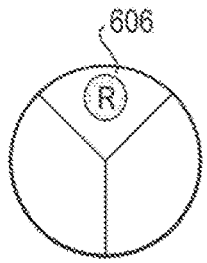
Figure 7A:
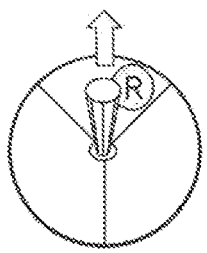
Figure 7B:
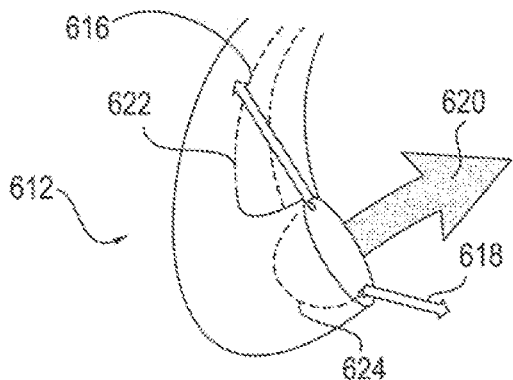
FIG. 7B is a perspective view of an articulating distal portion of a catheter and top views of the controllers of FIGS. 6A and 6C, illustrating user input corresponding to a different direction of articulation of the distal portion, according to one embodiment.
Figure 7B:
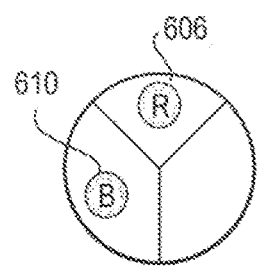
Figure 7B:
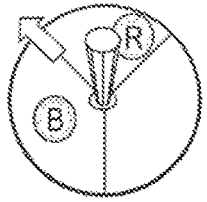

FIGS. 7A and 7B illustrate equivalent button and joystick control inputs that would cause a catheter 612 to articulate toward a red wire 622 (FIG. 7A) and in between the red wire 622 and a blue wire 624 (FIG. 7B). For example, FIG. 7A shows a catheter 612 responding to a single control button push or joystick movement in the direction of red 606 and consequently pulling or tensioning the red wire 622 represented by the red indicator 614, thereby articulating the catheter 612 in the direction of the large arrow 620. Alternatively, FIG. 7B illustrates the catheter 612 responding to a simultaneous red and blue button 606, 610 press or the joystick moving in between the red and blue 606, 610 graphics. Simultaneously actuating controls 606 and 610 will trigger corresponding wires 622 and 624 (e.g., represented by virtual indicators 616, 618) to pull or tension, resulting in articulation of the catheter 612 in the direction of the large arrow 620. While some embodiments may have a separate color button for each wire on the catheter 612, an alternative embodiment may involve a bend button and a rotate button with colors of the wires identified on the rotate button. In this embodiment, the user would use the rotate button to orient with the required color and then press the bend button to bend in the required direction. This has the advantage of not requiring a bend button for each wire on the circumference of the catheter.

Figure 8A:
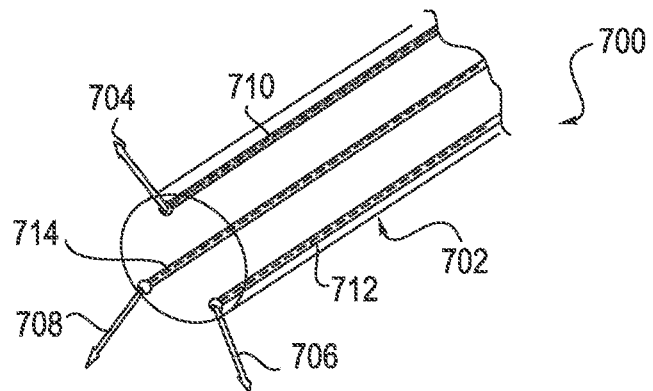
FIG. 8A is a perspective view of a catheter with a virtual indicator overlay, according to one embodiment.
Figure 8B:
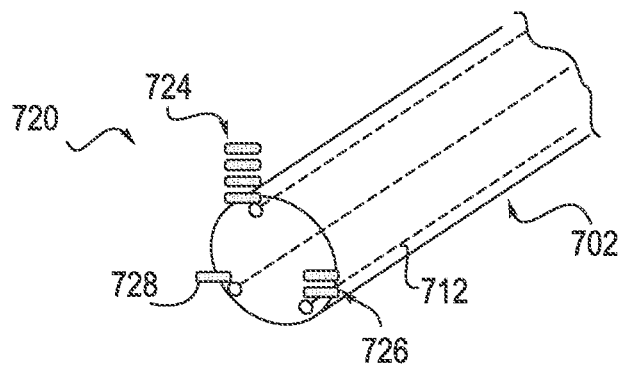
FIG. 8B is a perspective view of a catheter with a virtual indicator overlay having a stacked bar configuration, according to an alternative embodiment.
Figure 8C:
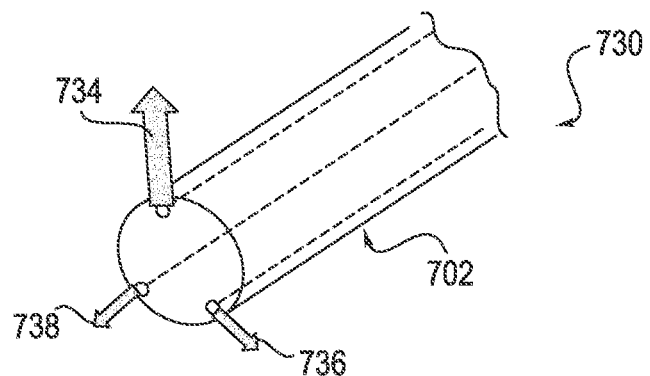
FIG. 8C is a perspective view of a catheter with a virtual indicator overlay having arrows with variable magnitude, according to another alternative embodiment.

Referring now to FIGS. 8A-8C, alternative embodiments of a visual display 700, 720, 730 may be used to illustrate movement of a catheter 702, for example to enhance instinctive navigation of the catheter 702. In the embodiment of FIG. 8A, the visual display 700, virtual indicators 704, 706, 708 are superimposed on a fluoroscopic image of the catheter 702, In order to easily identify which wire is controlled by which control (e.g., buttons or action of the joystick), identifiers for each wire are displayed near or superimposed onto the tip of the catheter. In one embodiment, a red indicator 704, a green indicator 706, and a blue indicator 708 are overlaid or superimposed onto three control wires 710, 712, and 714, respectively. The virtual overlay indicators 704, 706, 708 likewise match the colors of the controls discussed above, indicating their one-to-one relationship (e.g., the control-to-wire relationship is fixed throughout the procedure, such that a particular control will always cause a particular wire to be pulled). Further, the indicators 704, 706, 708 are intuitive and easily distinguishable, so that the operator may immediately recognize the indicator 704, 706, 708 (and consequently the corresponding pull wire) upon glancing at it.

In some embodiments, a view of the catheter may change during a procedure or use case. In some embodiments, a catheter orientation or position may be indicated in a first or second view of the catheter using one or more methods, for example shading or coloring of the catheter based on the depth of the catheter into the viewing plane away from the user or 3-D viewing technology that may be manipulated (e.g., rotated, magnified) to view the catheter from one or more directions. In some such embodiments, the virtual indicator may automatically change and update based on the current view. For example, if the controls are labeled "green" for left and "blue" for right in a first view, the virtual indicators may be exchanged such that "green" still means left and "blue" still means right in a second view, for example if the catheter has rolled or twisted in the second view.

In some embodiments, the first view may be instinctive while the second view is not instinctive. In some such embodiments, a focus, gaze, or attention of a user may be tracked, for example by a camera, to determine which view the user is using, such that the instinctiveness of the view relies on whether the user is using that particular view. Alternatively, the system may force the user to use, for example, only the first view as their primary view by either changing the size of the view or changing the on-screen indicators, such that first view is the instinctive view.

Furthermore, in addition to being color coordinated, the overlay virtual indicators 704, 706, and 708 may be extended or enlarged to demonstrate the load on the wire (e.g., an amount or duration of force placed on the wire), which may serve as an important metric in determining whether the patient's anatomy is restricting movement. For example, the operator may compare the control effort (e.g., the magnitude of the virtual indicator) with the actual articulation amount of the catheter to determine if a patient's anatomy is restricting the movement of the catheter.

FIG. 8B illustrates another embodiment, in which a visual display 720, uses stacked bar indicators 724, 726, 728, with variable magnitude representing differing wire loads. FIG. 8C illustrates another embodiment of a visual display 730, in which arrow indicators 734, 736, 738 have differing magnitudes representing differing wire loads. Either or both of the embodiments illustrated in FIGS. 8B and 8C may also be used with the embodiment of the visual display 700 illustrated in FIG. 8A. A bar or arrow with greater magnitude represents the load on the wire, which is correspondingly greater. Accordingly, the operator may thereby minimize unwanted damage to vessel walls by observing the changing magnitude of the virtual indicator and comparing the actual movement of the catheter. If the magnitude is great and the movement is minimal, the operator may conclude that the catheter is being restricted by the patient's anatomy. Additionally or alternatively, the user interface may be configured to provide a tactile feedback indicating that the catheter is being restricted by the patient's anatomy (e.g., the joystick vibrates upon being obstructed).

Predictive User Interface for Instinctive Catheter Control

In some embodiments, the user interface 124 may be configured to receive an operator input and command the movement of a virtual representation, e.g., a virtual indicator, overlaying an image of a flexible catheter, for example generated by a processor. In some embodiments, the virtual indicator does not represent the current articulation direction of the elongate member, but rather indicates which movement the catheter would make, if the motors/drivers where engaged, e.g., a predictive virtual representation. The predictive virtual indicator may overlay or otherwise be superimposed over an actual image of the catheter (e.g., via medical imaging such as fluoroscopy, thermography, magnetic imaging, ultrasonography, computed tomography, positron emission tomography, etc.). The virtual indicator may be aided in tracking the catheter in the image using computer vision techniques to process the image and determine the catheter location.

Figure 9A:
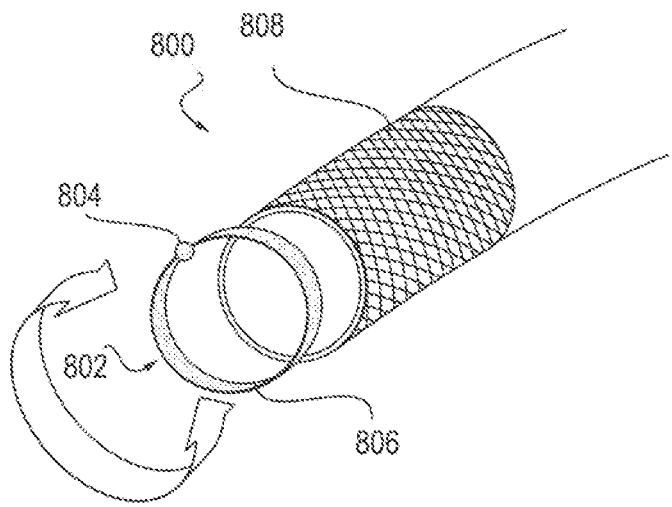
FIG. 9A is a perspective view of a distal portion of a catheter with a virtual indicator overlay having a ring-and-bead configuration, according to one embodiment.
Figure 9B:
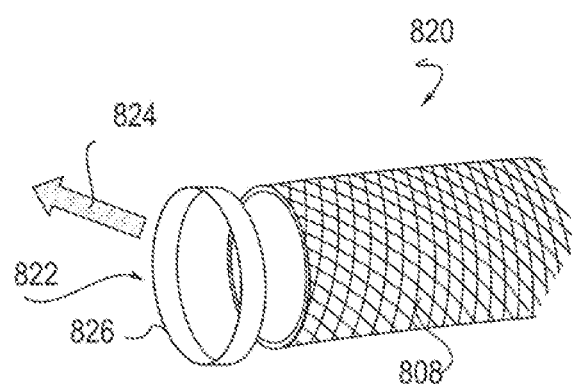
FIG. 9B is a perspective view of a catheter with a virtual indicator overlay having a ring-and-arrow configuration, according to an alternative embodiment.

Referring now to FIGS. 9A and 9B, two alternative embodiments of virtual indicator overlays 802, 822 on images 800, 820 of a distal portion of a catheter 808 are illustrated. In the embodiment shown in FIG. 9A, the virtual indicator overlay 802 is a graphic symbol including a bead 804 on a ring 806. The position of the bead 804 along the ring 806 indicates a bend direction of the catheter 808, and the bead 804 may move around the circumference of the ring 806, as indicated by the double-pointed arrow. In another embodiment, as illustrated in FIG. 9B, the image 820 may include a virtual indicator overlay 822 that includes a ring 826 and an arrow 824. The arrow 824 may indicate bend directionality in a way that is similar to that of the bead 804 and may similarly move around the circumference of the ring 826. In some embodiments, the arrow 824 may also grow and/or shrink in size to indicate the amount of commanded bending signal (e.g., the amount of bend commanded by the user via a user input). As shown in FIGS. 9A and 9B, the bead 804 or arrow 824 virtual indicator represents the direction the catheter 808 would articulate if the controller were engaged. Stated alternatively, the predictive virtual indicator 802, 822 uses available elongate member or catheter roll information to notify the operator of the imminent articulation direction before the elongate member 808 is articulated.

Importantly, the predictive virtual indicator overlay 802, 822 may instruct the operator whether the catheter 808 is pointing into or out of the screen when the elongate member 808 is positioned in a plane perpendicular to the visual display 128. It can be very difficult to decipher whether the elongate member 808 is pointing into or out of the visual display 128. In some embodiments, the direction in which the ring or arrow virtual indicator 822 rolls in relation to direction of the controller input may determine whether the elongate member 808 is pointing into or out of the screen in a plane perpendicular to the visual display 128.

For example, as shown in FIGS. 10A and 10B, the bead 804 (or arrow 834 in an alternative embodiment) on the predictive indicator 802 may roll in the opposite direction of the controller input if the elongate member 808 is pointed out of the visual display 128 (e.g., the elongate member 808 is facing towards the operator). For example, FIG. 10A illustrates the elongate member 808 pointing into the visual display when the predictive virtual indicator 804 rolls in the same direction as that of a joystick 838 (e.g., both roll clockwise). Alternatively, FIG. 10B illustrates the elongate member 808 pointing out of the visual display, because the predictive virtual indicator 804 rolls in a direction opposite of the joystick 838 (e.g., controller rolls clockwise and the predictive indicator rolls counterclockwise). Accordingly, the operator can easily decipher the heading of the elongate member 808 without actually articulating the elongate member 808 and thus potentially harming the patient's vasculature.

In some embodiments, the visual display 128 (FIGS. 1A and 1B) may be in communication with a processor (not shown). The processor may generate the virtual indicator 802 overlaid on an actual image of a catheter 808 inserted into the patient's anatomy. The processor may be configured to adjust or manipulate the virtual indicator 802 to indicate which direction the catheter 808 would articulate if the controller were engaged. Further, the processor may be operable to dynamically determine the desired articulation direction of the catheter (e.g., which wire(s) to pull/tension and which wire(s) to relax) based on the bead/arrow position on the virtual indicator 802. A non-transitory medium (not shown) storing a set of instructions may include one or more instructions to superimpose the virtual indicator 802 on the tip of the catheter 808 and one or more instructions for allowing the operator to rotate the virtual indicator 802 circumferentially around an axis. Additionally, the set of instructions may further include one or more instructions for allowing the user to manipulate multiple controls to move the catheter/elongate member 808, and may include a set of instructions for using kinematic information or sensor data (e.g., FOSSL, electromagnets), for example, to orient, position, and coordinate the virtual indicator 802 with the catheter 808. The virtual indicator 802, therefore, advantageously uses available catheter 808 roll information to notify the operator of the imminent articulation direction before the catheter 808 actually articulates. Accordingly, the operator is encouraged or expected to interact with the virtual indicator 802 and visual display 128 to fine-tune the orientation of the virtual bead or arrow.

Once the catheter 808 is actually articulated, the virtual indicator 802 will show the actual movement of the catheter 808. Thus, the indicator 802 not only shows the user how the catheter 808 will (or should) articulate before actual articulation, but it also shows the user how the catheter 808 actually articulates.

Referring now to FIGS. 11A and 11B, in some embodiments, the controller 844 may include multiple controls, such as a first control 842 configured to roll/rotate the predictive indicator, a second control 846 configured to articulate the elongate member 808, and a third control 848 configured to relax the elongate member 808. As shown in FIGS. 11A and 11B, the first control 842 may include a control column or joystick. Alternatively, in some embodiments, the first control 842 may be a touch sensitive pad. The first control or joystick 842 may be configured to rotate or roll while in the upright or vertical position which correspondingly controls the rotation of the bead or arrow on the ring of the virtual indicator. In some embodiments, the joystick 842 is a position controller and rotating the joystick 842 in the clockwise direction would roll the bead/arrow of the virtual indicator in the same direction (unless, however, if the elongate member is pointing out of the screen, in which case the bead/arrow would roll opposite the direction of the rotation of the joystick 842). It should be noted that in some embodiments, the catheter is not actually "rotated" or "rolled" in response to a command to "rotate" or "roll," but is progressively articulated using pull wires to mimic a rotational movement. For example, if a command is provided to articulate the catheter to the right, the system pulls or tensions a wire to articulate the catheter to the right. Subsequently, if the bead/arrow is rotated 180 degrees and the same articulation button is depressed, the system understands that the bead/arrow has been rotated, and in response pulls or tensions another wire to articulate the catheter to the left. In short, the system may dynamically decide which wire to pull/tension and relax based on the bead/arrow location on the virtual indicator. Further, in this example, the catheter does not physically roll/rotate, but rather the virtual indicator rotates in the visual display. As mentioned, the system 100 is configured to determine the articulation direction (and consequently the respective wire(s) to actuate and relax) in response to the position of the bead/arrow on the virtual indicator. Therefore, the system 100 reduces operator error and minimizes inadvertent touching of vessel walls.

The joystick 842 may likewise be configured to tilt forward and backward to command the elongate member to insert or retract, respectively. That is, the joystick 842 is a rocker switch but with added granularity allowing finer motion control. The joystick 842 may be spring loaded so that the joystick 842 returns to its upright/vertical, middle position when no external force is applied. The control input (e.g., tilting for insert/retract and/or the rate of return back to the middle position) may be mapped to the rate of increase or decrease as in velocity control. For example, tilting the joystick 842 fully forwards or backwards may insert/retract the elongate member at a greater velocity than slightly tilting the joystick. The rate at which the joystick 842 returns without external force, however, may be a constant velocity.

In some embodiments, the controller 844 may likewise include multiple push controls, for example a second control 846 and a third control 848. For example, the second control 846 may be configured to articulate the elongate member, while the third control 848 may be configured to relax the elongate member (e.g., an articulation button and a relax button). For example, once the direction is set in which the elongate member would articulate via the joystick 842 (e.g., rotating the bead/arrow), pressing the second control 846 button will physically articulate the elongate member in the set direction. The elongate member may continue to articulate until the force is lifted from the first control 842 (e.g., until the operator releases the articulate button). Further, pressing and holding the third control 848 will gradually relax the elongate member back to its straight configuration. Thus, the elongate member may remain in its articulated configuration until the third control 848 is pressed to relax the elongate member.

Referring now to FIG. 12, an alternative embodiment of a controller 904 may include a joystick 910, a bend button 912, a relax button 914, a roller 916 and a light feature 918. The roller 916 (or "fourth control") may act as a locking feature (or alternatively another form of failsafe mechanism in alternative embodiments), to ensure there is no accidental activation of roll or insertion activities. The roller 916 may be operable to rotate and correspondingly rotate the bead/arrow virtual indicator. Thus, the joystick 910 may be configured to move forward and backward for insertion and retraction, respectively. Alternatively, the joystick 910 may be configured as a toggle button, in which the entire joystick 910 can be pushed down from the top to either activate or deactivate the locking feature. With the roll lock enabled, the roller 916 may still be operable to rotate but without having any effect on the virtual indicator, and hence no change in articulation direction. However, even with the locking feature, the roller 916 may still be used for combining the insertion and roll of the elongate member (e.g., simultaneous actions) by merely disabling/deactivating the lock feature. The controller 904 base may also include the light feature 918 or other indicator, for example a circular area around the base of the controller 904 embedded with different colors to indicate whether the lock has been enabled.

Figure 13:
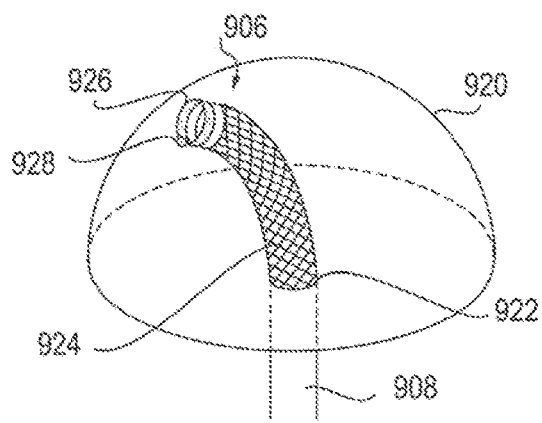
FIG. 13 illustrates a distal portion of a catheter with a virtual dome constraining the motion of the catheter, according to one embodiment.

Referring now to FIG. 13 illustrates an image of a dome 920 at a distal end of the elongate member 908. The dome 920 may represent a constraint for the catheter 908 tip so that at least part of the catheter 908 tip is required to be on a surface of the dome 920 regardless of how the catheter 908 is driven. In one embodiment, the catheter tip motion is confined to a surface of the virtual dome 920 created around a base 922 of its articulation section 924, and a 3D joystick (not shown), for example, would navigate the catheter tip around the dome's surface. According to one example, the circumference of the dome 920 may expand depending on the exposed length of the catheter's articulation section (e.g., a telescoping catheter). Alternatively, the full length of the articulation section may be used to set the size of the dome 920.

A virtual ring 926 may be a projection of the catheter tip onto the dome 920 surface and the bead/arrow 928 indicates which direction the ring would move if the controller were engaged. Accordingly, the virtual indicator 906 is always on the dome 920 surface. Pressing the articulation button as described above would move the catheter 908 tip in the direction towards the bead/arrow 928 along the dome 920 surface.

Figure 14A:
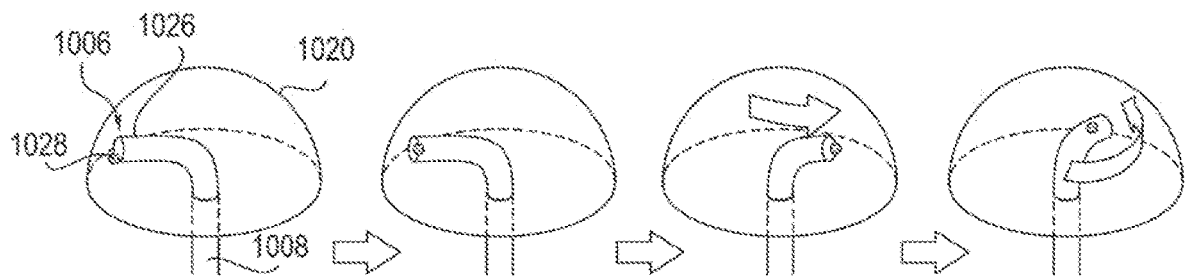
FIGS. 14A and 14B illustrates the motion of the distal portion of the catheter enclosed by the virtual dome of FIG. 13.
Figure 14B:
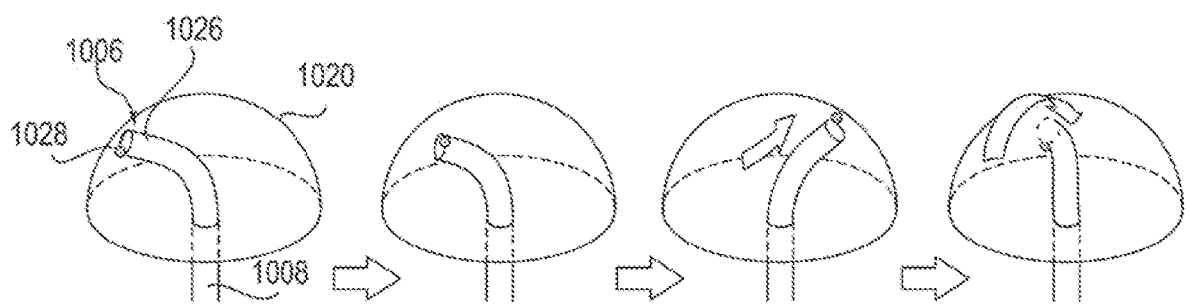

For example, FIG. 14A illustrates a response of the catheter 1008 when the virtual indicator 1006 is rolled ninety (90) degrees in clockwise direction prior to the user pressing the articulation button. (The direction of rotation, in this embodiment, is from the perspective of inside of the catheter 1008. An observer outside the catheter 1008 would view this rotation as appearing counter clockwise.) When the articulation button is pressed, the ring 1026 moves along the surface of the dome 1020 following the direction of the bead 1028. If the virtual indicator 1006 is rolled forty five (45) degrees more, pressing the articulation button would initially roll and relax the catheter 1008 at the same time, but the catheter 1008 would eventually articulate away from the user, for example as shown in FIG. 14B. This can be seen in FIG. 14B, illustrating the successive roll/relax and roll/articulate events. For example, the catheter 1008 relaxes as the tip or ring 1026 straightens and moves towards the top of the dome 1020, but the articulating angle subsequently increases as the ring 1026 moves further way from the dome 1020 apex. Thus, the relax control button may be redundant as the operator can always roll the indicator 1006 a hundred and eighty (180) degrees and press the articulation button to relax the catheter 1008. However, the separate control button may make it easier to access this important function, as pressing relax would always bring the catheter 1008 tip back to the top of the dome 1020 following the shortest path regardless of roll and articulation.

Figure 15A:
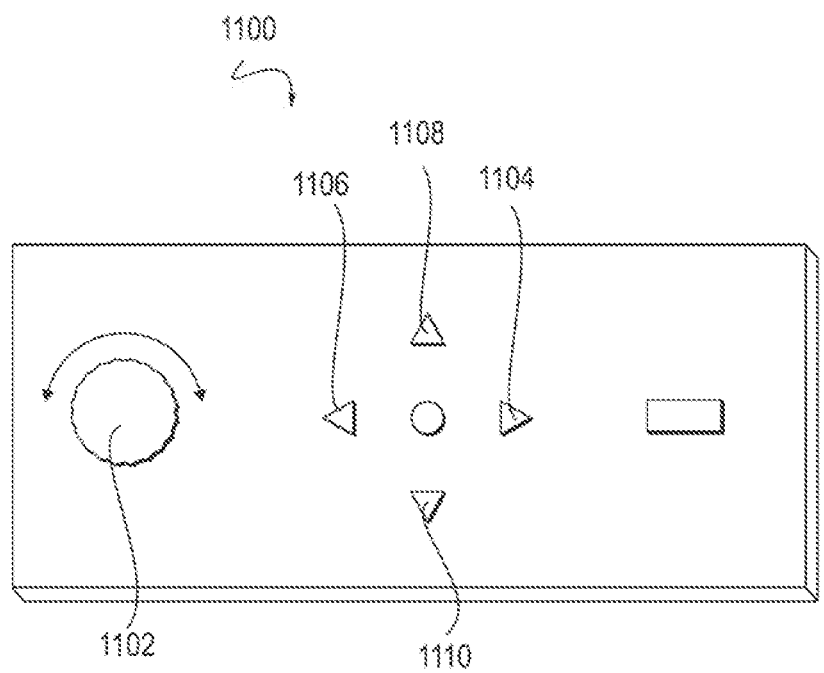
FIGS. 15A and 15B are top views of a controller of the user interface of FIG. 1B, according to another alternative embodiment.
Figure 15B:
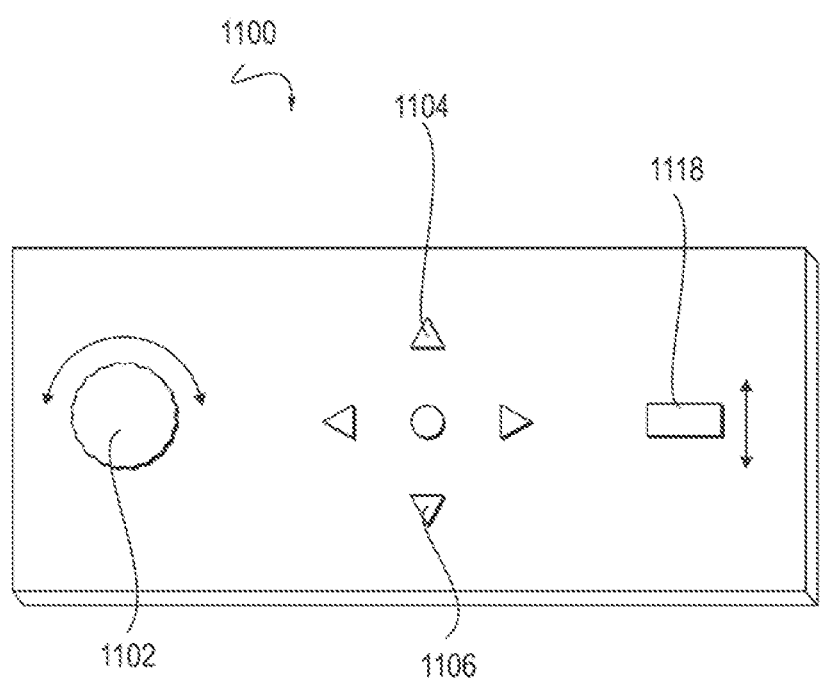

The virtual dome implementation may use the same physical controller as illustrated in FIG. 11A, 11B, or 12 (e.g., a 3D joystick with articulate/relax control buttons). Alternatively, FIG. 15A illustrates a controller 1100 according to another example. The controller 1100 may have a roll knob 1102, four control buttons for articulating 1104, relaxing 1106, inserting 1108, and retracting 1110. The controller 1100 illustrated in FIG. 15B is similar in that the roll knob 1102 is the same, but the right and left buttons would be disabled such that the up/down buttons may be used for articulating and relaxing, respectively. A switch or slider 1118 may be operable to move back and forth for inserting and retracting.

Roll Compensation for Instinctive Catheter Control

Figure 16:
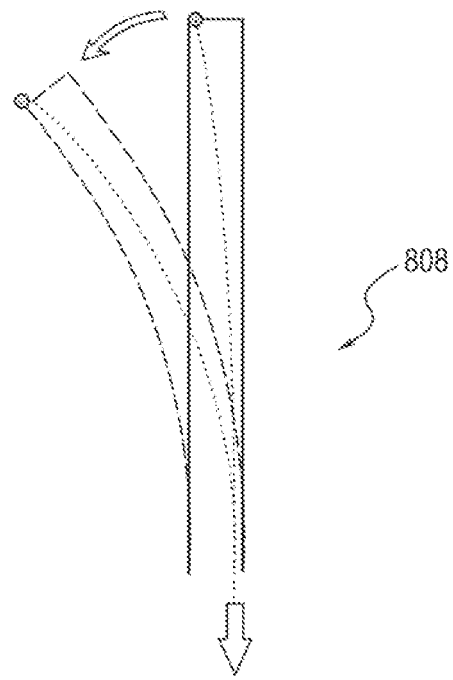
FIG. 16 is a side view of a distal portion of a catheter, illustrating an effect of distal roll on a catheter with 180 degrees twist.

Previously, a catheter was presumed to not rotate or roll around its axis as it advances through the vasculature. However, this presumption is not true in reality. For example, as shown in FIG. 16, a distal section of a catheter 808 is illustrated with a 180 degree twist. When the controller desires to articulate the catheter to the right, it pulls the wire on the right side of the catheter 808. However, instead of articulating to the right, the catheter 808 may articulate to the left because of the roll or twist experienced by the catheter 808. Previously, the controller could not make proper adjustments to correct the action because there was no concept of catheter roll. However, as will be described in further detail below, a roll sensor may be used to enable roll compensation and correction.

A roll sensor has the potential to improve the catheter driving experience by enabling the controller to adapt to the inevitable twist or roll in the catheter shaft as it is navigated through the vasculature. For example, the controller may change an amount of wire pull or tension based on the roll angle in order to articulate the catheter tip in the desired direction. In some embodiments, this is achieved by altering the desired articulation direction by the measured roll amount.

Figure 17A:
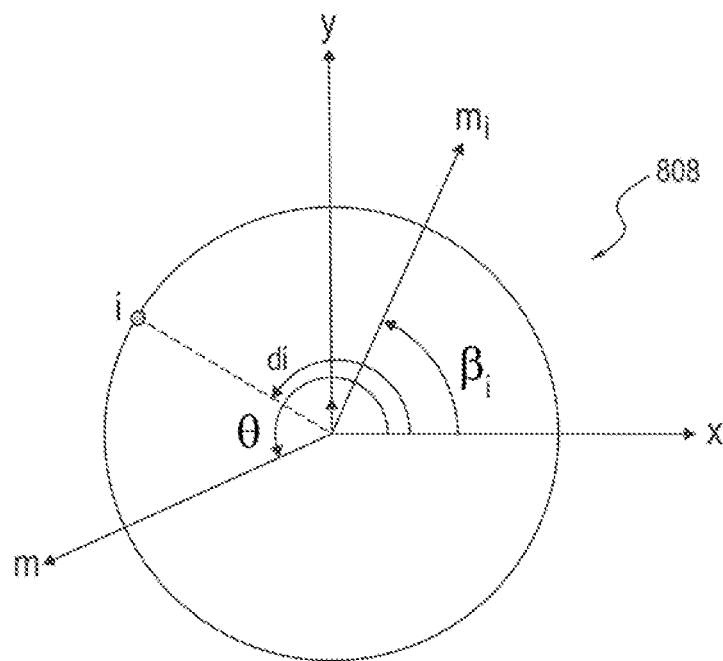
FIGS. 17A and 17B are end-on and perspective views, respectively, of a distal portion of a catheter, illustrating moments of movement on a catheter tip, according to one embodiment.
Figure 17B:
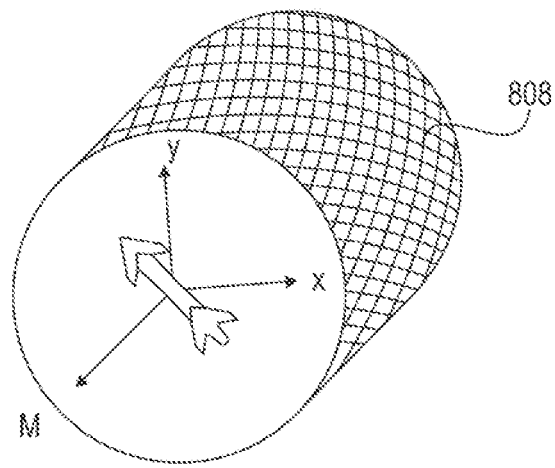

Referring now to FIGS. 17A and 17B, when an articulation command is initiated, the controller first computes the moment required to articulate the catheter tip and then calculates how much to pull or tension the wire to generate the moment. FIGS. 17A and 17B show moments and various angles involved in the computation. If M is the desired moment and $m_i$ is the moment generated from pulling the $i^{th}$ wire in the catheter, the following equation describes how the desired moment is related to the moments resulting from wire pulls.

$$M(\theta) = A(\beta_1, \beta_2, \ldots )m \quad (1)$$

$$\begin{bmatrix} M_x \\ M_y \end{bmatrix} = \begin{bmatrix} \cos\beta_1 & \cos\beta_2 & \ldots \\ \sin\beta_1 & \sin\beta_2 & \ldots \end{bmatrix} \begin{bmatrix} m_1 \\ m_2 \\ \vdots \end{bmatrix} \quad (2)$$

As shown in FIG. 17A, θ is the direction of the moment M, and $\beta_i$ is the direction of the moment resulting from the $i^{th}$ wire pull. The $\beta_i$ is related to the angular position of the $i^{th}$ wire, $\alpha_i$, by a fixed amount π/2. To compute the new articulating moment direction, the measured roll angle, γ, is subtracted out from the original articulating moment direction θ to compensate for the roll. As such, a new articulating direction, θ*, is calculated according to the following rule:

$$\theta^* = \theta - \gamma \quad (3)$$

FIGS. 18A-23B illustrate systems and methods for integrating a magnetic encoder into a catheter for measuring its roll. These FIGS. 18A-23B are illustrated from the perspective of being inside of the catheter—e.g., as if a camera were inside the catheter and looking out through an opening in the distal tip of the catheter. The instrumented catheter would enhance the instinctive driving experience by further improving the accuracy of catheter control.

Figure 18A:
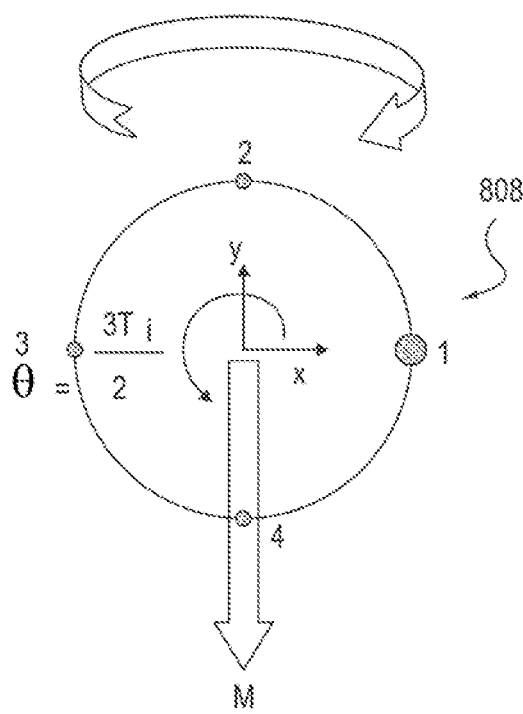
FIGS. 18A and 18B are end-on views of a distal portion of a catheter, illustrating roll compensation for no roll and 90 degrees roll, respectively, according to one embodiment.
Figure 18B:
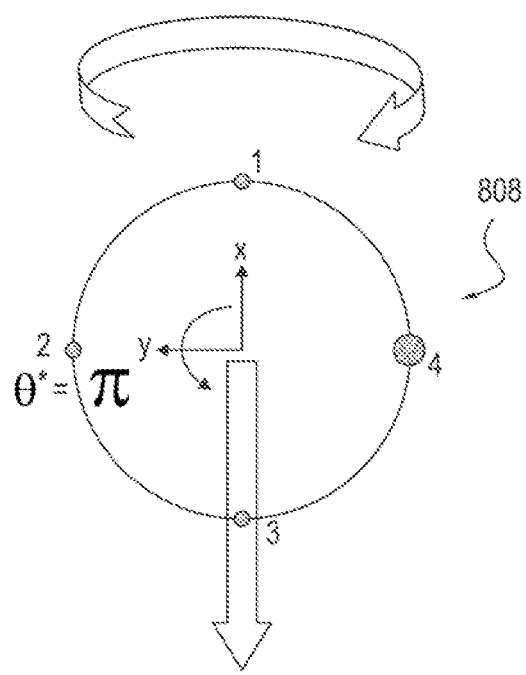

For example, FIGS. 18A and 18B illustrate a case where $\gamma$ is $\pi/2$, which means the distal tip of the catheter rolled 90 degrees in the counter clockwise direction. The rotation is around the z-axis, which points out of the screen according to the right hand rule, i.e. cross x-axis and y-axis to get the z-axis. FIG. 18A illustrates a scenario in which there is no roll. For example, an incoming command directs the controller to articulate the catheter to the right, that is $\theta=3\pi/2$, and the controller would pull wire 1 on the right side of the catheter. With a 90 degree roll on the catheter, pulling the same wire 1 would not articulate the catheter to the right because wire 1 is now at the top of the catheter. Alternatively, a compensated controller would have a new articulating moment direction $\theta^*=\pi$ as shown in FIG. 18B and this would enable the controller to pull the correct wire, for example wire 4, to produce an articulation to the right.

Figure 19A:
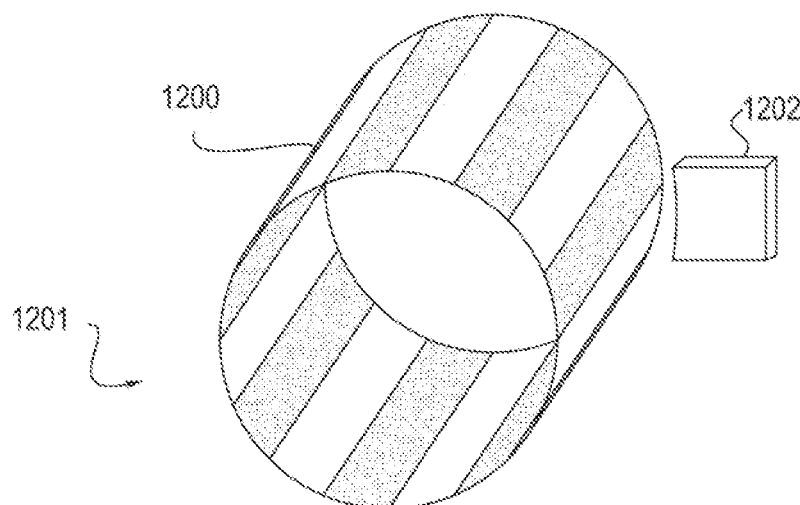
FIGS. 19A and 19B are perspective and end-on views, respectively, of a magnetic encoder that uses a Hall-effect or magneto-resistive sensor to detect changes in polarity, according to one embodiment.
Figure 19B:
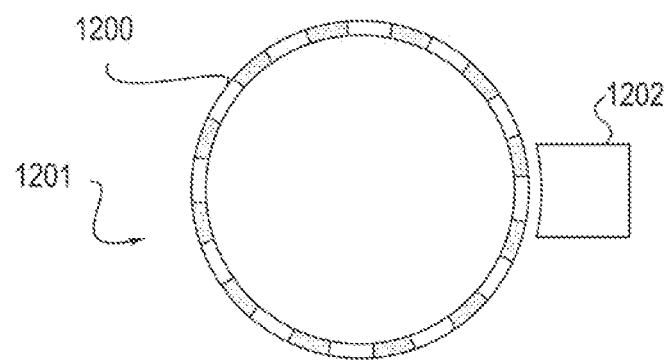

Referring now to FIGS. 19A and 19B, in some embodiments, one or more encoders 1201 may be used to measure catheter roll and thus improve instinctive driving. In general, encoders are non-contact sensors with an infinite number of turns. Encoders come in optical and magnetic varieties. The optical encoder uses an optical emitter-detector pair with a patterned encoder wheel in between to detect the amount of rotation. Alternatively, a magnetic encoder 1201, shown in FIGS. 19A and 19B, uses a Hall-effect or magneto-resistive sensor 1202 to detect changes in polarity. Instead of an encoder wheel, a magnetized ring 1200 is used to provide the alternating magnetic poles along the circumference of the ring 1200. The Hall-effect sensor 1202 can detect the change in polarity as the ring 1200 turns, and the sensor 1202 produces electric pulses for angular measurements. A magnetic encoder 1201 measures relative roll between the magnetic ring 1200 and the Hall-effect sensor 1202, i.e. the read head. Typically, the sensor 1202 is fixed to a stationary object, and the magnetized ring 1200 rotates with the spinning object or vice versa.

Figure 20A:
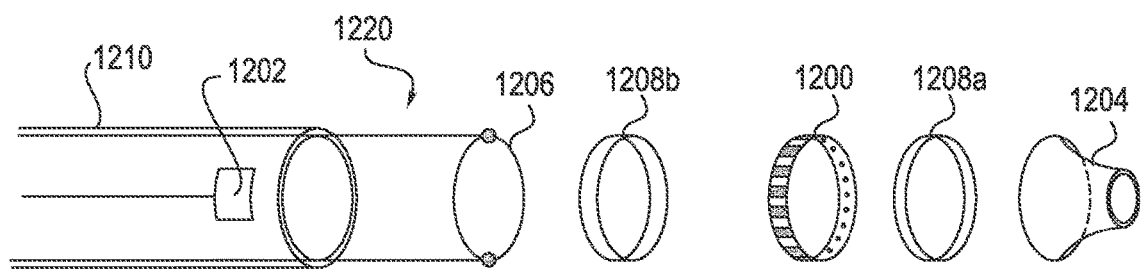
FIGS. 20A and 20B are exploded and assembled/side views, respectively, of a distal portion of a catheter including the magnetic encoder components of FIGS. 19A and 19B, according to one embodiment.
Figure 20B:
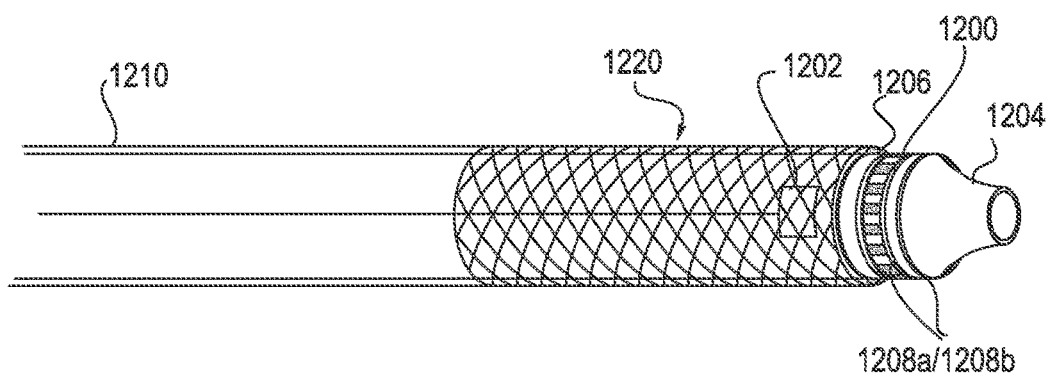

Referring now to FIGS. 20A and 20B, the magnetic ring 1200 and the sensor 1202 may be incorporated into a catheter 1220, which may also include a distal catheter tip 1204, two rings 1208a, 1208b on either side of the ring 1200, a control ring 1206 and control wires 1210. The magnetic ring 1200 functions to rotate whenever the catheter 1220 rolls, so that the Hall-effect sensor 1202 can detect the change in roll. The ring 1200 is mounted on rails 1208a, 1208b on both sides to allow it to spin around freely as the catheter 1220 rolls, and the sensor 1202 is fixed and embedded into the catheter wall. In one embodiment, as shown in FIG. 20A, the control ring 1206 provides soldering points for the control wires 1210. Alternatively, the control ring 1206 and the proximal rail 1208b may be combined into a single ring to simplify catheter construction, and the control wires 1210 may be directly soldered to the proximal rail 1208b.

In some embodiments, a fluid bearing rather than a mechanical bearing may be used to enable the ring 1200 to freely rotate under gravitational pull in the case in which the rails 1208a, 1208b cannot significantly reduce friction. For example, the magnetized ring 1200 may be enclosed in a sealed, tube-like structure filled with low viscosity fluid to lower the friction. The operation of the Hall-effect sensor 1202 would not be affected, because it does not need to be in direct contact with the ring 1200. Alternatively, small-scale dithering may be used to constantly break friction. In some embodiments, a sound wave or any other type of external excitation signal may be used to excite the ring 1200 to break free from either the rail 1208a, 1208b or the fluid bearing.

Figure 21A:
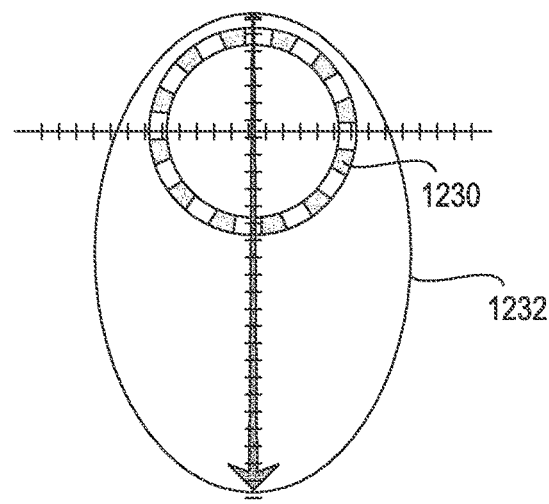
FIGS. 21A and 21B are end-on views of a magnetic ring of a magnetic encoder, illustrating asymmetrical weight of the ring, according to one embodiment.
Figure 21B:
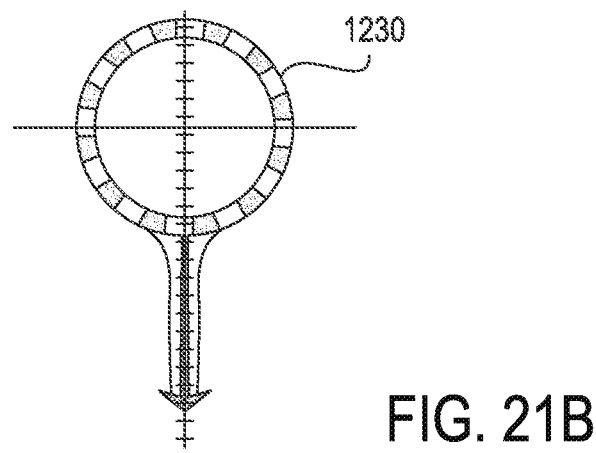

Referring now to FIGS. 21A and 21B, in some embodiments, to achieve ring rotation when the catheter rolls, a ring 1230 may be constructed with unbalanced weight distribution, so that it stays upright regardless of catheter roll. As shown in FIGS. 21A and 21B, the ring 1230 is heavy on one side and light on the other side. Thus, the ring may rotate independently to keep the heavy side down consistently. The size of an enclosing oval 1232, as shown in FIG. 21A, demonstrates the weight distribution in the ring 1230. The weight gradually increases from the top side of the ring to the bottom side of the ring 1230, as designated by the double-headed arrow. In some embodiments, the weight distribution may change abruptly. In some embodiments, a discontinuous weight change, for example extra weight hanging from one side of the ring 1230, may maintain the ring 1230 stay upright consistently.

In some embodiments, a roll sensor may improve the control and navigation of a robotic catheter. The controller may be able to interpret user inputs quickly, based on the measured roll information and adjust its control output accordingly to increase instinctive driving of the catheter. The catheter may be articulated in the direction desired by the user with all the computation hidden from the user.

Alternatively or additionally, a roll sensor may be used for navigation with direct visualization. For example, a camera may be installed on the distal end or tip of a catheter to directly provide a visual image of the surroundings during navigation. For example, U.S. patent application Ser. No. 13/452,029 (U.S. Pub. No. 2012/0296161), filed Apr. 20, 2012, has further information regarding a method to obtain a clear viewing field for a camera, and the contents of this application are hereby incorporated by reference in their entirety.

Further, in some embodiments, a roll sensor may measure the absolute roll of the catheter and may be applied to a non-telescoping catheter. If the catheter is instrumented with a camera, the roll sensor can help reorient the camera view so that it displays the field of view right side up. For example, the camera view may not rotate even if the camera itself rotates, and one or more catheter controls may compensate for the catheter roll so that the catheter is manipulated instinctively under the endoscopic camera view.

Figure 22A:
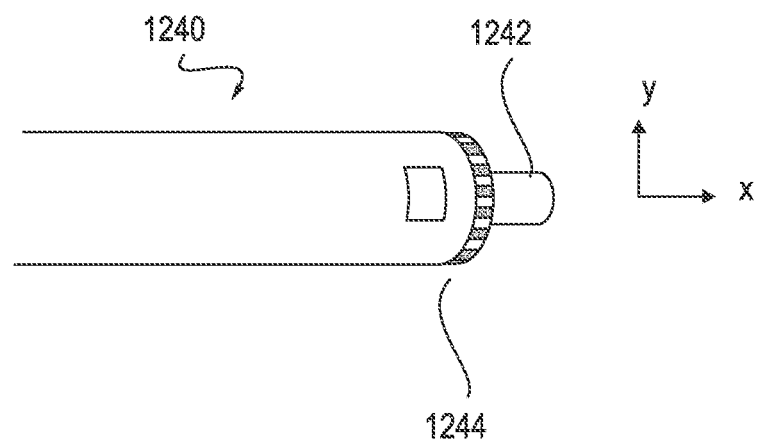
FIG. 22A is a perspective view of a distal portion of a catheter with a distal tip camera, according to one embodiment.
Figure 22B:
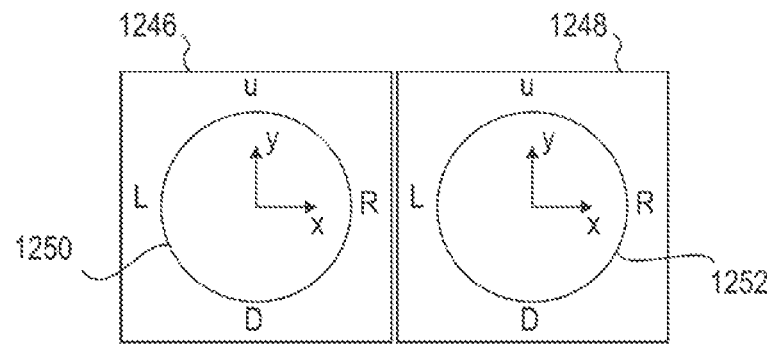
FIG. 22B is a front view of two video displays illustrating image representations of the catheter of FIG. 22A, illustrating what a user would see on the screen when the catheter is equipped with a camera for zero degrees roll.
Figure 23A:
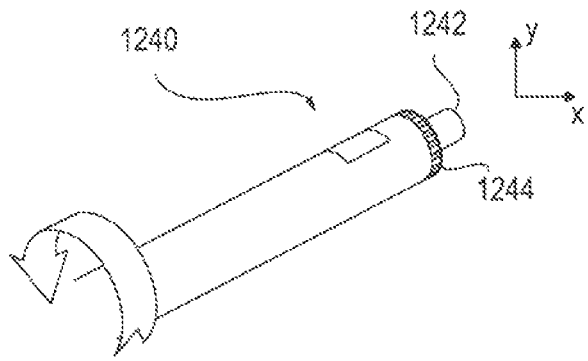
FIG. 23A is a perspective view of a distal portion of a catheter with a distal tip camera, according to one embodiment.
Figure 23B:
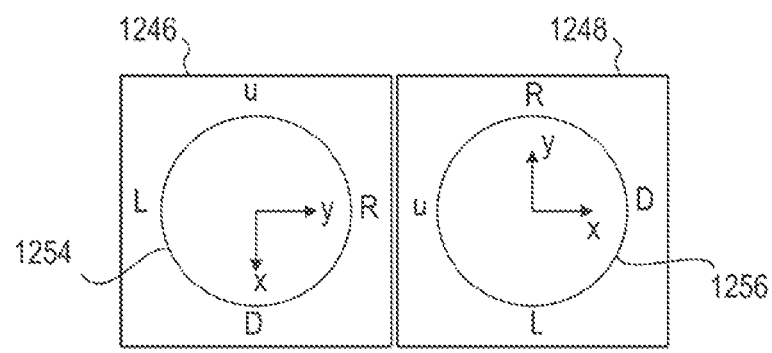
FIG. 23B is a front view of two video displays illustrating image representations of the catheter of FIG. 23A, illustrating what a user would see on the screen when the catheter is equipped with a camera for 90 degrees roll.

FIGS. 22A and 23A illustrate a catheter 1240 from the viewpoint of a user. The catheter 1240 is equipped with a camera 1242 at its distal tip and a roll sensor 1244 just proximal to the camera 1242. FIG. 23A illustrates the catheter 1240 rolling 90 degrees in a counter clockwise direction (flat, curved arrow). FIGS. 22B and 23B illustrate a left viewing screen 1246 and a right viewing screen 1248, which display images 1250, 1252, 1254, 1256 to the user to assist in manipulation of the catheter 1240. In FIG. 23B, the image 1254 on the left screen 1246 is an uncompensated view, and the image 1256 on the right screen 1248 is a compensated view (e.g. to keep the right side of the catheter 1240 up). The camera view on the left 1254 rotates as the camera 1242 rolls, whereas the view on the right 1256 remains the same independent of camera roll. Further, the catheter controller may recognize the change in roll and make proper adjustments to facilitate navigation. This is illustrated as the D instead of R in the right image 1256 in FIG. 23B. When it was R, as shown in the image 1252 in FIG. 22B, pulling the R wire would articulate the catheter 1240 to the right. Due to the catheter/camera roll, the relationship has changed and now the controller needs to pull the D wire instead of the R wire to articulate the catheter 1240 to the right. This modification in control algorithm is transparent to the user, and the controller would make the proper adjustment based on the roll measurement.

In some embodiments, a magnetic encoder and sensor may be placed respectively on components of a telescoping catheter, such that relative roll between inner and outer components of the telescoping catheter can be determined. For example, a roll sensor may provide relative roll measurements between the camera, and therefore the instrumented balloon catheter, and the guide catheter. Instead of the absolute roll measurement, $\gamma$, as described above, this embodiment uses a relative roll measurement, $\delta$, to obtain a new articulating direction $\theta^r$. This new articulation direction makes navigation intuitive from the camera's perspective. $\delta$ measures the roll of the guide catheter with respect to the camera.

$$\theta^r = \theta - \delta \tag{4}$$

For example, with respect to $\delta$ measurements, when the camera up direction aligns with the guide catheter's up direction, the relative roll measurement, $\gamma$, is zero; likewise, if the camera rolls $\pi/2$ counter clockwise, it is equivalent to the guide catheter roll of $-\pi/2$ counter clockwise.

Figure 24A:
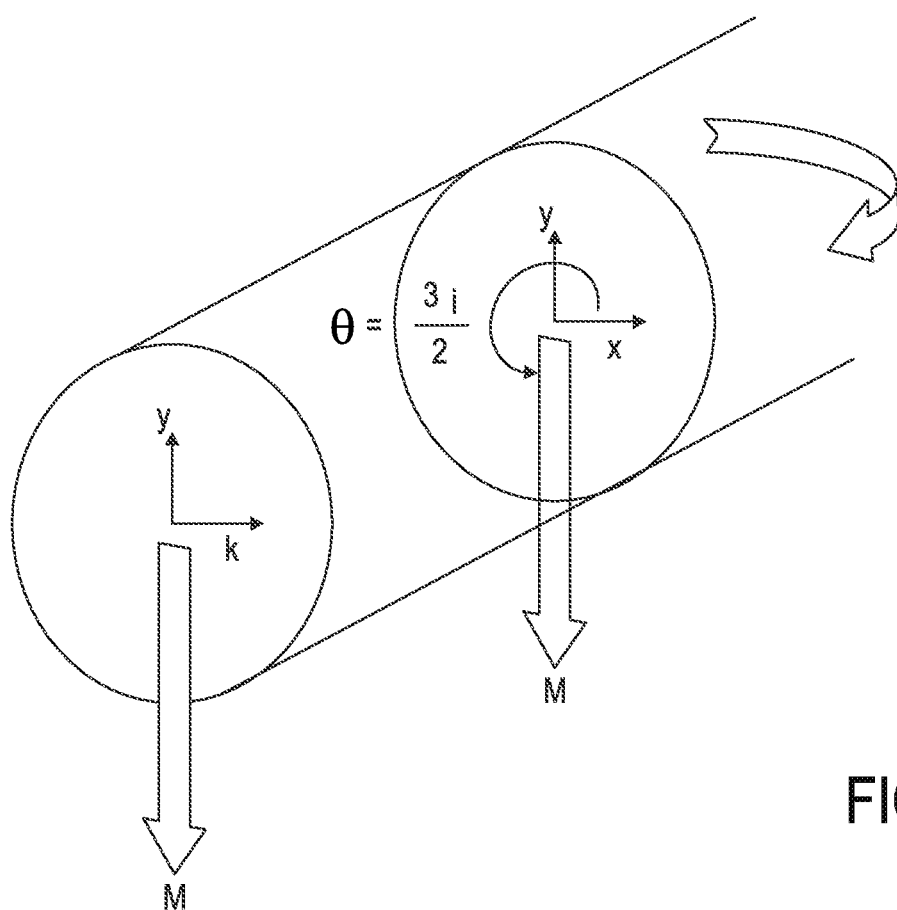
FIGS. 24A and 24B are perspective diagrammatic representations of a distal end of a catheter, illustrating roll compensation for no camera roll and 90 degrees camera roll, respectively, according to one embodiment.
Figure 24B:
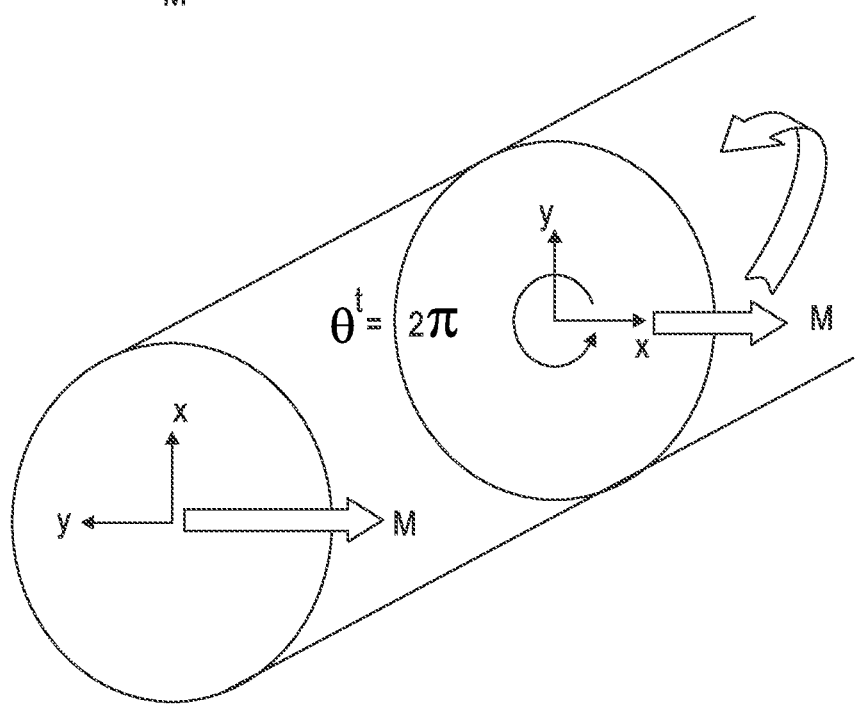

For example, FIGS. 24A and 24B illustrate a case where the camera is rolled 90 degrees but the catheter roll remains unchanged. The front image in FIGS. 24A and 24B is a camera view, and the back image in FIGS. 24A and 24B is a catheter view. Both FIGS. 24A and 24B describe a user action to articulate the catheter to the right as seen from the camera. Notice the direction of M vector changing as the camera rolls. If the catheter is commanded to articulate right in the camera view, the articulating moment should be generated in the downward direction, i.e. $\theta = 3\pi/2$. This is relatively straightforward in FIG. 24A, but when the camera rolls, the controller modifies the command according to Equation 4. The resulting direction as shown in FIG. 14B is $\theta^r = 2\pi$ and the catheter would articulate up as the top wire becomes active. Notice that this would make the catheter articulate right in the current camera view. From the user's point of view, pressing the right button on the pendant makes the catheter articulate right in the camera view.

The above discloses a concept presented here that is for use of instrumented catheters equipped with a relative roll sensor to improve catheter control under direct visual feedback. With the help of such sensor, the user can instinctively drive the catheter while looking at the live video feed from the camera. The visual feedback is easy to interpret and intuitive to understand. As such, integrating catheter motion with camera posture is believed to be an important step toward creating a truly immersive and instinctive catheter driving experience.

Figure 25A:
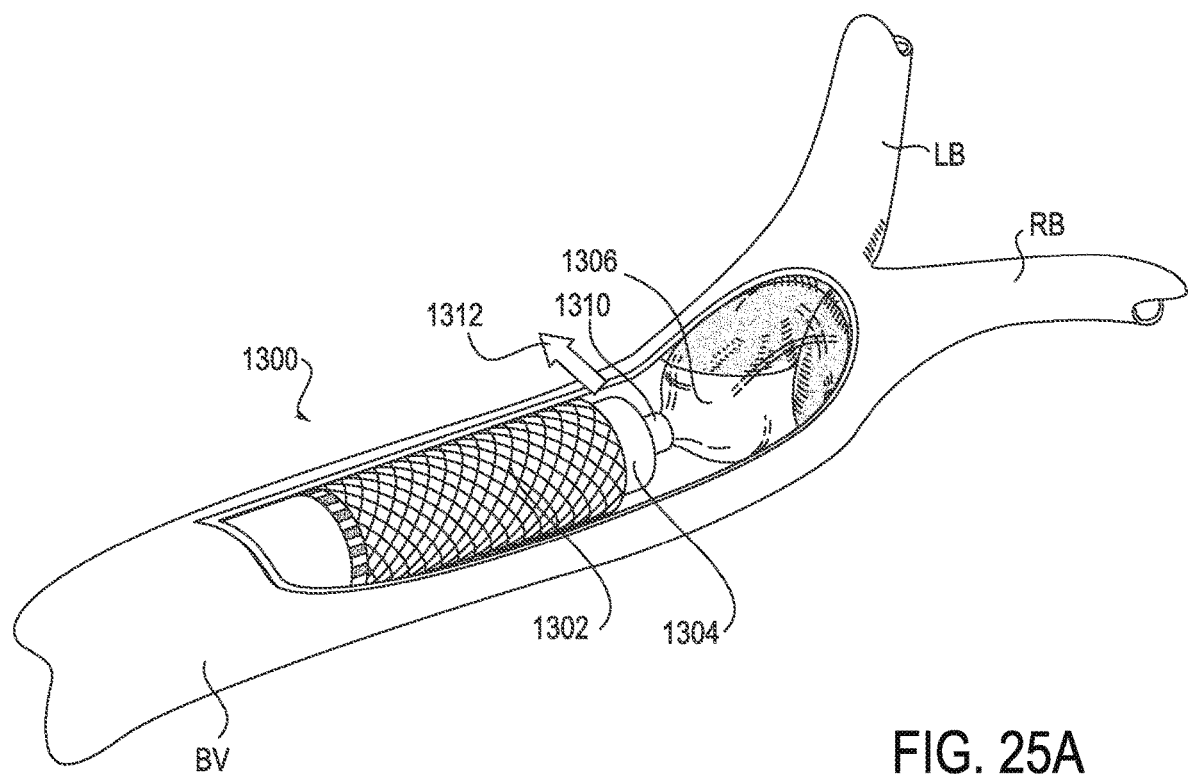
FIGS. 25A and 25B are perspective and end-on views of a catheter system, illustrating a simulated usage of a camera and a guide catheter.
Figure 25B:
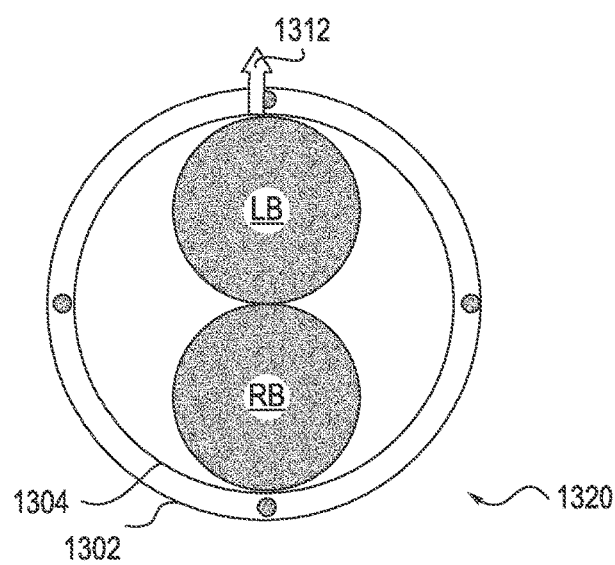

Referring now to FIGS. 25A and 25B, a simulated usage of a catheter-based system 1300 for navigating and performing a procedure in a blood vessel is illustrated. The system 1300 is shown advanced through a blood vessel BV toward a branching of the vessel BV into a left branch LB and a right branch RB. The system 1300, in this embodiment, includes a guide catheter 1302 and an instrumented balloon catheter 1304, which includes a distal tip camera 1310 and a balloon 1306. The system includes roll compensation, as disclosed herein. An image 1320 (FIG. 25B) may be provided, for example to show directionality of the camera 1310, such as a camera-up arrow 1312.

The user interface may use a computer or a computer readable storage medium implementing the operation of drive and implementing the various methods described herein. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The exemplary illustrations are not limited to the previously described examples. Rather, multiple variants and modifications are possible, which also make use of the ideas of the exemplary illustrations and therefore fall within the protective scope. Accordingly, it is to be understood that the above description is intended to be illustrative and not restrictive.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "an," "the," etc. should be read to recite one or more of the indicated elements unless a claim recites an explicit limitation to the contrary.

What is claimed is:

1. A robotic catheter system, comprising:
   a flexible catheter having a proximal end, a distal end, and an articulating portion at the distal end;
   a roll sensor coupled with the flexible catheter at or near the distal end to detect rotation of the distal end of the flexible catheter around a longitudinal axis of the flexible catheter, the roll sensor configured for insertion into a patient when at least the distal end of the flexible catheter is inserted into the patient;
   a visual display for displaying an image of at least part of the flexible catheter;
   a processor for generating a virtual indicator displayed on the image of the at least part of the flexible catheter, wherein the virtual indicator indicates at least one of a direction of articulation or an amount of articulation of the articulating portion of the flexible catheter; and
   a controller coupled with the proximal end of the flexible catheter to receive a first user input and a second user input, the controller configured to:
      determine an articulating moment for roll compensation based on an adjusted articulating moment direction, the adjusted articulating moment direction determined based on the detected rotation;
      cause, via the processor, the virtual indicator to show, based on the articulating moment and the first user input, the adjusted articulating moment direction before the flexible catheter articulates; and
      articulate the articulating portion of the flexible catheterbased on the second user input and the articulating moment,
   wherein the controller comprises a first control configured to receive the first user input and rotate the virtual indicator about a longitudinal axis of the flexible catheter in response to the first user input, without rotating the flexible catheter.

2. The system of claim 1, wherein the first control comprises a control column configured to rotate about an axis relative to a base of the controller, wherein rotation of the virtual indicator corresponds to rotation of the control column.

3. The system of claim 2, wherein rotating the control column in a clockwise direction rotates the virtual indicator in a clockwise direction when the flexible catheter points into the visual display, and rotating the control column in the clockwise direction rotates the virtual indicator in a counterclockwise direction when the flexible catheter points out of the visual display.

4. The system of claim 1, further comprising an actuator coupled to the flexible catheter for articulating the articulation portion, wherein the controller comprises a second control coupled to the actuator for articulating the articulation portion.

5. The system of claim 1, wherein the virtual indicator corresponds to the controller, wherein inputting the second user input into the controller causes the processor to generate the virtual indicator indicating a direction of movement of the articulation portion of the flexible catheter.

6. The system of claim 1, wherein the virtual indicator corresponds to an actuator coupled to the flexible catheter, wherein engaging the actuator articulates the articulating portion in a direction of the virtual indicator.

7. The system of claim 6, further comprising a plurality of graphic symbols, the plurality of graphic symbols comprising a first graphic symbol, a second graphic symbol, and a third graphic symbol, wherein the actuator comprises a plurality of actuators, the plurality of actuators comprising a first actuator, a second actuator, and a third actuator, wherein the virtual indicator includes the first graphic symbol corresponding to the first actuator coupled to the flexible catheter, the second graphic symbol corresponding to the second actuator coupled to the flexible catheter, and the third graphic symbol corresponding to the third actuator coupled to the flexible catheter, and wherein the plurality of graphic symbols are equally spaced along a circumference of the image of the at least part of the flexible catheter displayed on the visual display.

8. The system of claim 7, wherein the plurality of graphic symbols comprise at least one of arrows or stacked bars.

9. The system of claim 7, wherein the controller includes multiple controls corresponding to the plurality of graphic symbols and coupled to the plurality of actuators, the multiple controls including the first control, wherein engaging the first control articulates the flexible catheter in a direction of the first graphic symbol, engaging a second control bends the flexible catheter in a direction of the second graphic symbol, and engaging a third control bends the flexible catheter in a direction of the third graphic symbol.

10. The system of claim 9, wherein engaging the first control and the second control simultaneously articulates the articulating portion of the flexible catheter in a direction between the first and second graphic symbols.

11. The system of claim 9, wherein the multiple controls and corresponding graphic symbols are color coded.

12. The system of claim 7, wherein each of the plurality of graphic symbols is configured to change in size in proportion to an amount of articulation of the flexible catheter in a direction of each of the plurality of graphic symbols.

13. The system of claim 1, wherein the virtual indicator comprises at least one graphic symbol selected from the group consisting of an arrow, stacked bars, a ring-and-bead, and a ring-and-arrow.

14. The system of claim 1, wherein the controller includes a joystick.

15. The system of claim 1, wherein the processor is configured to track the flexible catheter in the image using computer vision techniques.

16. The system of claim 15, wherein the processor is operable to overlay the virtual indicator on the image in response to tracking information.

17. The system of claim 1, wherein the controller is configured to determine the articulating moment based on: determining an initial articulating moment direction; and subtracting the detected rotation from the initial articulating moment direction to determine the adjusted articulating moment direction.

18. A method for facilitating a robotic catheter procedure, the method comprising:
displaying an image of at least part of a flexible catheter on a visual display, the flexible catheter having a proximal end, a distal end, and an articulating portion at the distal end;
generating, via a processor, a virtual indicator displayed on the image of the at least part of the flexible catheter, wherein the virtual indicator indicates at least one of a direction of articulation or an amount of articulation of the articulating portion of the flexible catheter;
inserting the distal end of the flexible catheter into a patient, wherein a roll sensor coupled with the flexible catheter at or near the distal end is inserted into the patient when at least the distal end of the flexible catheter is inserted into the patient;
detecting, via the roll sensor, rotation of the distal end of the flexible catheter around a longitudinal axis of the flexible catheter;
determining, via a controller coupled with the proximal end of the flexible catheter to receive a first user input and a second user input, an articulating moment for roll compensation based on an adjusted articulating moment direction, the adjusted articulating moment direction determined based on the detected rotation;
causing, via the processor, the virtual indicator to show, based on the articulating moment and the first user input, the adjusted articulating moment direction before the flexible catheter articulates;
articulating, via the controller, the articulating portion of the flexible catheter based on the second user input and the articulating moment; and
rotating, via a first control of the controller configured to receive the first user input, the virtual indicator about a longitudinal axis of the flexible catheter in response to the first user input, without rotating the flexible catheter.

19. The method of claim 18, further comprising providing a user input device for receiving the second user input to control articulation of the articulating portion of the flexible catheter, wherein the user input device corresponds to the virtual indicator.

20. The method of claim 18, further comprising articulating the flexible catheter in the direction of the virtual indicator, in response to the second user input.

21. The method of claim 18, wherein the virtual indicator comprises at least one graphic symbol selected from the group consisting of an arrow, stacked bars, a ring-and-bead, and a ring-and-arrow.

22. The method of claim 18, wherein the virtual indicator correlates to an actuator coupled to the flexible catheter.

23. The method of claim 22, further comprising engaging the actuator to articulate the articulating portion of the flexible catheter in the direction of articulation.

24. The method of claim 22, further comprising changing a size of the virtual indicator in response to and in proportion to the amount of articulation of the articulating portion of the flexible catheter in the direction of articulation.

25. The method of claim 18, further comprising tracking the flexible catheter in the image, using computer vision techniques, to generate tracking information, wherein the tracking information is used to overlay the virtual indicator on the image.

26. The method of claim 18, further comprising registering the image of the flexible catheter with a fluoroscopic image of the flexible catheter to generate registration information, wherein the registration information is used to overlay the virtual indicator on the image.

* * * * *